United States Patent [19]
Fiers et al.

[11] Patent Number: 5,962,298
[45] Date of Patent: Oct. 5, 1999

[54] INFLUENZA VACCINE

[75] Inventors: Walter Charles Fiers, Destelbergen; Tom Marie Deroo, Kuurne; Willy Alfons Min Jou, Destelbergen, all of Belgium

[73] Assignee: Vlaams Interuniversitair Instituut Voor Biotechnologie, Zwijnaarde, Belgium

[21] Appl. No.: 08/669,496

[22] PCT Filed: Jan. 6, 1995

[86] PCT No.: PCT/BE95/00002

§ 371 Date: Sep. 27, 1996

§ 102(e) Date: Sep. 27, 1996

[87] PCT Pub. No.: WO95/18861

PCT Pub. Date: Jul. 13, 1995

[30] Foreign Application Priority Data

Jan. 11, 1994 [NL] Netherlands ............................ 9400045
Jan. 24, 1994 [EP] European Pat. Off. .............. 94200159

[51] Int. Cl.$^6$ .............................. C12N 9/26; C12N 15/00; C07H 21/04
[52] U.S. Cl. ....................... 435/201; 435/320.1; 536/23.2
[58] Field of Search .................................. 435/200, 240.2, 435/320.1; 536/23.2; 424/94.6, 325; 935/22

[56] References Cited

U.S. PATENT DOCUMENTS 4,861,864  8/1989  Atkinson et al. ........................ 530/324

OTHER PUBLICATIONS

Van Rompuy et al. (1982) Complete Nucleotide Sequence of a Human Influenza Neuraminidase Gene of Subtype N2 (A/Victoria/3/75), J. Mol. Biol. 161: 1–11, Sep. 1982.
Rudinger J. (1976) Characteristics of the amino acids as components of a peptide hormone sequence, In: Peptide Hormones, Ed. J. A. Parsons, pp. 1–7, Jun. 1976.
Parks et al. (1990) Folding an oligomerization properties of a soluble and secreted form of the paramyxovirus hemagglutinin–neuraminidase glycoprotein. Virology 178: 498–508, Oct. 1990.
Castrucci et al. (1993) Biologic importance of neuraminidase stalk length in influenza A virus. J. Virology 67 (2): 759–764, Feb. 1993.
Paterson et al. (1990) Conversion of a classII integral membrane protein into a soluble and efficiently secreted protein: Multiple intracellular and extracellular oligomeric and conformational forms. J. Cell Biology 110: 999–1011, Apr. 1990.

Laver (1978) Crystallization and peptide maps of neuraminidase "heads" from H2N2 and H3N2 influenza virus strains. Virology 86: 78–87, Jan. 1978.

Chemical Abstract, vol. 111, No. 1, Jul. 3, 1989, Columbus, Ohio: Abstract No. 4171q. Marina Els et al., "Sialic acid is cleaved from glyconjugates at the cell surface when influenza virus neuraminidases are expressed from recombinant vaccinia viruses." p. 403. & Virology vol. 170, No. 1, 1989, pp. 346–351.

Chemical Abstracts, vol. 116, No. 9, Mar. 2, 1992, Columbus, Ohio: Abstract No. 77462y, Ulrike Weyer et al., "A baculovirus dual expression vector derive from the *Autographa californica* nuclear polyhedrosis virus polyhedrin and p10 promoters: co–expression of two influenza virus genes in insect cells." p. 209, & J. Gen. Virol., vol. 72, No. 12, 1991, pp. 2967–2974.

Chemical Abstracts, vol. 118, No. 3, Jan. 18, 1993, Columbus, Ohio: Abstract No. 17169q, Karen Mather et al., "Expression of influenza neuraminidase in baculovirus–infected cells" p. 165; & Virus Res., vol. 26, No. 2, 1992, pp. 127–139.

Chemical Abstracts, vol. 118, No. 9, Mar. 1, 1993, Columbus, Ohio: Abstract No. 77492z, Yuexin Lin et al., Expression of neuraminidase of influenza A virus in insect cells. p. 484, & Shengwu Huaxue Yu Shengwu Wuli Xuebao, vol. 24, No. 3, 1992, China, pp. 201–205.

*Primary Examiner*—Robert A. Wax
*Assistant Examiner*—Einar Stoel
*Attorney, Agent, or Firm*—Webb Ziesenheim Logsdon Orkin & Hanson, P.C.

[57] ABSTRACT

The present invention relates to a recombinant neuraminidase obtainable by culturing in a suitable culture medium host cells which are transformed with a neuraminidase expression vector or infected with a virus which is transformed with a neuraminidase expression vector, wherein the expression vector comprises at least a part of the coding region of a neuraminidase gene of an influenza virus minus the region which codes for the membrane anchor, or a modified version thereof, preceded in phase by a signal sequence; and isolating the expression product neuraminidase from the culture medium. The invention further relates to a vaccine in which the recombinant neuraminidase is applied, and methods for manufacturing and purifying thereof.

13 Claims, 17 Drawing Sheets

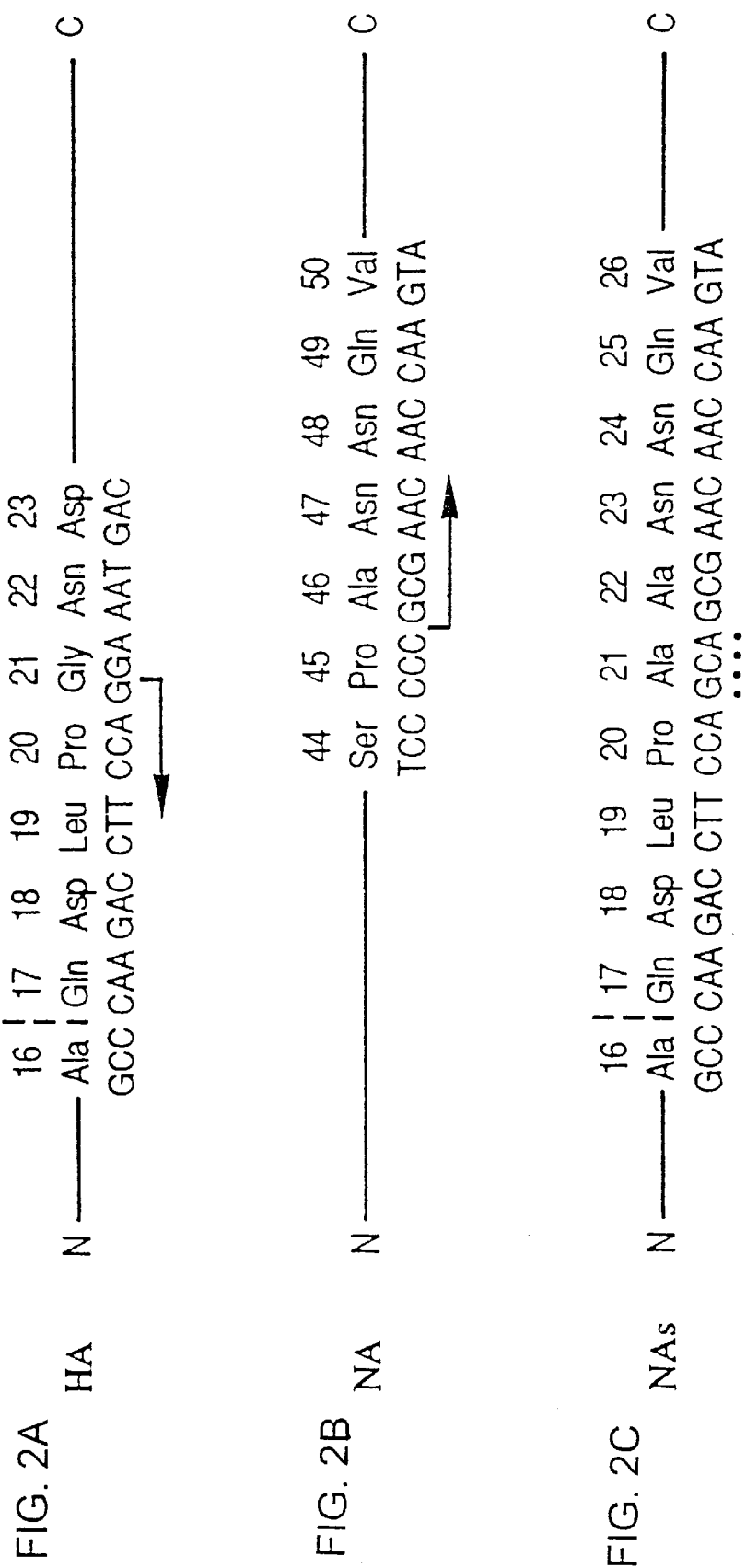

SEQUENCE LISTING (1) GENERAL INFORMATION:

(iii) NUMBER OF SEQUENCES: 1

(2) INFORMATION FOR SEQ ID NO: 1:

(i) SEQUENCE CHARACTERISTICS:
      (A) LENGTH: 11
      (B) TYPE: AMINO ACID
      (C) STRANDEDNESS: SINGLE
      (D) TOPOLOGY: UNKNOWN (xi) SEQUENCE DESCRIPTION: SEQ ID NO: 1:

Leu Glu Lys Arg Glu Ala Glu Ala Tyr Pro Lys
1               5                   10

INFLUENZA VACCINE

The present invention relates to a recombinant influenza neuraminidase, an expression vector with which the recombinant neuraminidase can be expressed in host cells, methods for producing and purifying recombinant neuraminidase, vaccines against influenza and the use of recombinant neuraminidase according to the invention.

Influenza A and B virus epidemics cause considerable discomfort to those affected and have a great influence on social and economic life. They cause a significant mortality rate in older people and in patients with chronic illnesses. Since their introduction during the 1940's, inactivated vaccines based on virus material cultured in chicken eggs have been found to be clearly effective against influenza infection and have resulted in a significant fall in the mortality rate of high-risk populations.

The influenza viruses are unique among the viruses of the bronchial tubes because they undergo a significant antigenic variation (so-called "drift") in their two surface antigens, that is, the hemagglutinin (HA) and the neuraminidase (NA).

In addition, influenza A in particular can escape the prevalent immunity due to the phenomenon of "shift". Appearing herein in the human virus is an NA gene which comes from the animal reservoir of influenza genes. In 1957 the NA1-type virus prevalent up to that time was thus replaced by a new NA2-type virus. Since 1977 the NA1-type viruses have also returned to the human population. The present vaccines must therefore preferably be aimed against both NA1 and NA2-type viruses.

NA catalyses the removal of terminal sialic acid residues of glycosyl groups whereby potential receptors for HA are destroyed (Gotteschalk, 1957; Burnet and Stone, 1947). It is assumed that NA is essential in preventing virus aggregation and in an efficient spreading from cell to cell (Colman and Ward, 1985).

Each NA molecule ($M_x$=240,000) has a toadstool-like structure which consists of four identical polypeptide chains built up of two dimers which are linked to disulphide bridges and in turn held together by non-covalent bonds (Bucher and Kilbourne, 1972; Laver and Valentine, 1969; Varghese et al., 1983; Ward et al., 1983). Otherwise than HA, NA is anchored in the lipid membrane by a non-spliced, NA-terminal, lipophilic sequence (Fields et al., 1983; Block et al., 1982), the so-called membrane anchor. The greatest part of the total structure protrudes above the membrane and forms there a distal, box-shaped "head" area localised on top of an elongate "stalk" region (Wrigley et al., 1973'). Inside the head each monomer has its own catalytic site and contains at least four NA-linked glycosyl groups (Colman et al., 1983; Ward et al., 1982). The presence of O-glycosylation has not yet been demonstrated up to the present time.

On account of their external localization the HA and NA antigens represent the most important viral target structures for the host immune system. Of antibodies which bind specifically to HA it is thought that they neutralise the viral infectivity, probably by blocking the early steps of infection (Hirst, 1942; Kida et al., 1983). NA-specific antibodies normally do not prevent the initial infection of a target cell (Jahiel and Kilbourne, 1966; Kilbourne et al., 1968; Johanssen et al., 1988) but precisely the spread of the virus. In addition, due to competition mechanisms, the immunologic response to NA appears to be partly suppressed in favour of the more frequently occurring HA antigen (Johanssen et al., 1987, Kilbourne, 1976). As net result the effect of NA immunity is generally overshadowed by the neutralising HA antibodies. For this reason the attention of vaccine designers has been focussed for a long time almost exclusively on HA.

A number of experimental observations indicate however that NA is indeed capable of playing a significant part in the build-up of protective immunity to influenza (Schulman et al., 1968; Johansen and Kilbourne, 1990; Johansen et al., 1993). Fundamental studies into the immunogenic potential of NA necessitate the availability of very pure antigens in sufficient quantities and with the correct three-dimensional conformation. Up until now NA has been prepared by treating viral envelopes with detergents (Gallagher et al., 1984; Kilbourne et al., 1968) or by proteolytic cleavage of the protein head, often by means of pronase (Seto et al., 1966; Rott et al., 1974), followed by purifying of the NA. Although to some extent usable, these methods have considerable limitations in respect of yield and purity.

It is therefore the object of the present invention to provide a recombinant influenza neuraminidase which has antigenic properties corresponding with the naturally occurring neuraminidase and is folded in the correct manner.

Such a recombinant neuraminidase in substantially isolated form can be obtained according to the invention by:

a) culturing in a suitable culture medium host cells which are transformed with a neuraminidase expression vector or infected with a virus which is transformed with a neuraminidase expression vector, wherein the expression vector comprises at least a part of the coding region of a neuraminidase gene of an influenza virus minus the region which codes for the membrane anchor, or a modified version thereof, preceded in phase by a signal sequence; and b) isolating the expression product neuraminidase from the culture medium.

The recombinant neuraminidase according to the invention which is secreted in the culture medium can for instance be used for fundamental studies, wherein the separate vaccination with NA is performed in order to determine the role of NA in a vaccine. In practice recombinant NA will however probably still be used in combination with HA in order to increase the degree of protection (percentage of the inoculated population that is effectively protected against an infection) and the protection persistence (protection against later epidemic strains).

More particularly the invention provides a recombinant influenza NA2 neuraminidase which can be obtained by culturing host cells in a suitable culture medium and isolating the expression product neuraminidase from the culture medium. This entails in practice for instance that a recombinant expression module from pAc2IVNAs is crossed in a wild-type baculovirus or a derivative thereof. Host cells are then infected with this recombinant baculovirus.

The host cells used for the production of the recombinant influenza neuraminidase preferably originate from lower eukaryotic organisms such as insects, preferably the insect cell line sf9, but can also be yeast cells such as Saccharomyces or Pichia.

The present invention further relates to two vectors for expressing a secretable influenza neuraminidase comprising a replication origin, at least a part of the coding region of the influenza neuraminidase gene minus the region which codes for the membrane anchor, or modified versions thereof, a signal sequence located at 5' from the coded region and coupled in phase thereto, a promoter located at 5' from the signal sequence and a transcription terminator located at 3' from the coding region. More particularly the invention provides a vector for use in expressing a secretable influenza NA2 neuraminidase comprising a replication origin, the coding region of the influenza NA2 neuraminidase gene of the virus strain A/Victoria/3/75 minus the region which codes for the membrane anchor, or modified versions thereof.

For expression in insect cells such a vector is placed in a cell together with a wild-type baculovirus or derivative thereof. A recombinant baculovirus results due to the occurrence of a double homologous recombination, wherein the expression module from the vector is introduced into the viral genome. After plaque purification a stock of recombinant baculoviruses is obtained which can subsequently be used to infect for instance Sf9-cells.

The signal sequence preferably originates from the hemagglutinin gene of the influenza NA2 virus A/Victoria/3/75 (H3N2). The invention preferably comprises the vector pAc2IVNAs, filed on 3 Jan. 1994 at the Laboratorium voor Moleculaire Biologie-Plasmidencollectie (LMBP), K.L. Ledeganckstraat 35, B-9000 Ghent, Belgium with the deposit accession number LMBP 2976, and used for transforming a virus, such as for instance the baculovirus, by means of double homologous recombination. Herein the expression module of the vector, consisting of the transcription regulation signals, the signal sequence and the coding region, is placed in the genome of the virus.

In another embodiment of the invention a second vector according to the invention is used. Such a vector is intended for use in yeast and comprises for instance a replication origin, the coding region of the influenza NA2 neuraminidase gene of the viral strain A/Victoria/3/75 minus the regions which code for respectively the membrane anchor and the stalk part of NA, or modified versions thereof, a signal sequence located at 5' from the coded region and coupled in phase thereto, a promoter located at 5' from the signal sequence and a transcription terminator located at 3' from the coding region.

The promoter and terminator sequences are preferably homologous and originate from the methylotrophic yeast *Pichia pastoris*, such as the alcohol oxidase I-gene sequences. The signal sequence is for instance the secretion signal of the prepro-mating factor a of *Saccharomyces cerevisiae*.

This vector pPP1IVNAfls was filed on 3 Jan. 1995 at the Laboratorium voor Moleculaire Biologie-Plasmidencollectie (LMBP), K.L. Ledeganckstraat 35, B-9000 Ghent, Belgium with the deposit accession number LMBP 3223.

The recombinant neuraminidase according to the invention is found to be able to generate a protective immunity against influenza viruses, particularly those of the NA2 type. The invention therefore also relates to a vaccine against influenza in which the recombinant neuraminidase is included.

The invention moreover relates to a method for manufacturing recombinant neuraminidase and a method for purifying same.

Referred to in the present description and claims by the term "NAs" is secretable (recombinant) neuraminidase. "pNA" refers to natural neuraminidase treated with pronase. "NA" means neuraminidase.

The present invention will be further elucidated with reference to the examples hereinbelow which are only intended by way of explanation and do not imply any limitation whatever in the scope of the invention.

EXAMPLE 1

Expression, Purification and Characterization of Recombinant Influenza NA2 Neuraminidase Materials and Methods 1. Construction of a Gene Which Codes for a Neuraminidase Which is Secreted and its Integration Into a Baculovirus Expression System a. Plasmides The plasmide pV6/21 is a pBR322 derivative containing a copy of the neuraminidase gene of A/Victoria/3/75 (H3N2) influenza virus (Van Rompuy et al., 1982). pSV51 and both pSV23m and pSV24m are respectively late and early SV40 replacement vectors and are described elsewhere (Huylebroeck et al., 1988). pSR S-8 is a plasmide based on pPLa2311 which contains the start sequence of the hemagglutinin (HA)-gene of A/Victoria/3/75 (H3N2) (Huylebroeck et al., 1988). The baculovirus transfer vector pVL941 was designed by Luckow and Summers (1989).

b. Subcloning of the HA Signal Peptide Sequence (pIVpreHA)

The 1830 bp BstNI fragment of pSR S-8 was filled in with Klenow-enzyme. PvuII-linkers (GCAGCTGC) were subsequently arranged. The resulting fragment and pBR322 were digested with PvuI and PvuII and the fragments of respectively 731 bp and 1699 bp were isolated. Ligation of these two produced pIVpreHA which contained the 5' non-translated region of the HA-gene, starting at $G_{-16}$ (ATG=+1, +2, +3), followed by the intact HA-signal peptide sequence and the first few codons of mature HA.

c. Construction of a Chimeric Sequence Which Codes for NA that Can Be Secreted: pATIVNAs pV6/21 was opened with PvuI and treated with Bal31 exonuclease. To this mixture were ligated HindIII-linkers, followed by digestion with HindIII. An NA-fragment of about 1500 bp was selected and cloned in the unique HindIII restriction site of pSV23m (pSV23mIVNA). Plasmides with the counter-clockwise insert were subsequently digested with FnudII en SalI and the 1291 bp fragment which contained the NA-gene minus the membrane anchor sequence was recovered. pIVpreHA was subsequently incubated with PstI and PvuII and the 861 bp fragment with the HA-signal sequence was retained. Both fragments were finally fused by PvuII-FnudII blunt ligation and inserted in the 2253 bp SalI/PstI fragment of pAT153, resulting in pATIVNAs. This plasmide carries the sequence which codes for the signal peptide of HA including the first few amino acids of mature HA, immediately followed by the NA-sequence lacking the signal peptide/membrane anchor and by a part of the region which codes for the "stalk".

Ligation of the HA and Na fragments resulted only in a single amino acid substitution (Gly to Ala), which corresponds with position 5 of mature HA. Based on the information published by Min Jou et al. (1988) and Van Rompuy et al. (1982), the predicted DNA- and amino acid sequences flanking the ligation site in NAs are shown in FIG. 2.

d. Integration of NA in a Baculovirus Transfer Vector

The 1368 bp XbaI/SalI fragment of pATIVNAs was ligated to the 5562 bp SalI/EcoRI fragment of PSV51 and the 624 bp EcoRI/XbaI fragment of pSV24m. A copy of the 1647 bp BamHI fragment containing the NAs gene and the SV40 poly(A)-site was subsequently inserted into the unique restriction site of pVL941, taking into account the correct orientation relative to the polyhedrine promoter, resulting in pAc2IVNAs. This construct enables an homologous recombination with wild-type AcNPV DNA after cotransfection of Sf9 cells. Recombinant virus descendants were isolated by successive plaque purification procedures as described by Summers and Smith (1987).

2. Insect Cell Culture—Production of NAs

For routine culture Sf9 insect cells were kept as confluent cell monolayers in TC100 medium with 10% foetal calf serum and 50 $\mu$g/ml gentamycine. For infection with the recombinant baculovirus the cultures were transferred to 200 ml suspensions growing in 850 cm$^2$ roller bottles (25 rpm). Suspension cells at the end of their log phase (2×10$^6$ cells/ml) were then infected with recombinant baculovirus at a moi ("multiplicity of infection", i.e. number of infective virus particles per cell) of 1.0. After two hours the infected cells were transferred to fresh serum-free TC100 medium and further incubated in suspension for 48 hours. NAs was purified out of the medium, as described below.

3. Growth of Influenza X-47 Virus

The influenza strain X-47 was used as source for the preparation of natural NA of A/Victoria/3/75 after treatment with pronase. The X-47 virus was cultured in the yolk bag cavity of 11 day-old embryo-containing chicken eggs. After two days incubation at 25 5° C. the eggs were cooled overnight at 4° C. and the yolk-bag fluid was harvested for further processing.

4. Buffer Systems

The following buffers were normally used:
buffer A: 20 mM diethanolamine/HCL pH 8.5;
buffer B: 50 mM NaAc, pH 5.5;
buffer C: 10 mm NaP, pH 7.4, 150 mM NaCl;
Buffers A and C contain in addition 4% butanol (except where indicated otherwise) and 2 mM CaCl$_2$.

5. Purification of NAs a. Ammonium Sulphate Fractionation

Sf 9 suspension cultures (normally about 1 liter) were harvested after inoculation (see above) and the cellular remnants were precipitated by centrifugation at 4,000×g for 15 minutes. All further treatments were performed at 4°. In the first purification steps 5 mM NaN$_3$ was added to the solutions. The cleared crude medium was subjected to ammonium sulphate fractionation at pH 7.5. Material that precipitated between 20% and 60% (NH$_4$)$_2$SO$_4$ was collected by centrifugation (10,000×g, 60 minutes) and dissolved in buffer A (without butanol)+20 mM NaCl in a quantity of $\frac{1}{10}^{th}$ the starting volume. The redissolved precipitation was dialysed (mwco ("molecular weight cut-off"): 25 kd) against 50 volumes of the same buffer for 24 hours, wherein the buffer was changed three successive times. Insoluble components were removed by centrifugation at 20,000×g for 15 minutes.

b. Sepharose Q-anion Exchange Chromatography

The dialysed solution was first supplemented to 4% butanol and subsequently placed on a Sepharose Q-column (2.5 cm×10 cm) which was equilibrated with buffer A+20 mM NaCl at a throughflow speed of 25 ml/hour. After washing of the column with the same buffer the elution was carried out with a linear NaCl concentration gradient in washing buffer to 250 mM (250 ml; 25 ml/hour). Fractions of each 2,5 ml containing NAs were identified by measuring the enzyme activity and the ELISA levels. The NA activity was eluated from the column as a single peak.

c. N-(p-aminophanyl) Oxamic Acid Agarose Affinity Chromatography

The use of this affinity matrix is described for the purification of (non-recombinant) influenza NA and bacterial NA-enzymes (Cuatrecasas and Illiano, 1971; Bucher, 1977). The correct functioning of the affinity matrix was only achieved by adapting the originally recommended buffer conditions. The active fractions after Sepharose Q-separation were collected and an equal volume of 200 mM NaAc pH 5.5 was added thereto. The active fractions were subsequently loaded onto an N-(p-aminophenyl) oxamic acid agarose column (1.5×5 cm) equilibrated in buffer B, 100 mM NaCl. The column was subsequently washed with equilibration buffer and desalted with buffer B. A second washing step was then performed with buffer A. The NAs were finally eluated by applying buffer A supplemented with 1 M NaCL at a throughflow speed of 10 ml/hour (fractions of 2 ml were collected).

d. Superdex 200 Gel Filtration Chromatography

The eluate of the affinity column was concentrated to 2.0 ml by making use of Centriprep™ concentrators (Amicon; mwco: 30 kd). The concentrate was then chromatographed in fractions of 1.0 ml sample volume on a Superdex 200 gel filtration column (1.5 cm×60 cm), which was equilibrated in buffer C with 4% butanol. The column was eluated in the equilibration buffer at a flow speed of 10 ml/hour and fractions of 1.0 ml were collected. For long-term storage at −20° C. related fractions were collected, concentrated, as described above, and subsequently supplemented with glycerol to an end concentration of 50%.

In order to estimate the molecular weight of purified proteins the gel filtration column was calibrated with apoferritin from the spleen of the horse (443 kd), β-amylase from the sweet potato (200 kd), alcohol dehydrogenase from yeast (150 kd), bovine serum albumin (67 kd) and carbonic anhydrase (2.9 kd) (all from Sigma Chemical Co.).

6. Preparation and Purification of pNA a. Treatment with Pronase

The yolk bag fluid of chicken eggs infected with X-47 was first cleared by centrifugation at low speed (1,000×g, 10 minutes) and then subjected to centrifugation at 13,000×g for 16 hours for precipitation of the virus. The viral precipitation was resuspended in 10 ml buffer C per equivalent of 100 infected eggs and pronase was added up to 2 mg/ml without any further purification of the virus. The mixture was incubated for 16 hours at 20° C. while being shaken lightly. Remaining virus cores and insoluble pronase components were subsequently removed by ultracentrifugation (100,000×g, 1 hour) at 4° C. The supernatant containing the released NA heads was then purified by column chromatography.

b. Sepharose β-cation Exchange Chromatography

The chromatographic procedures were carried out at 4° C. The crude pNA sample was diluted five times and brought to 50 mM NaAc pH 5.5, 2 mM $CaCl_2$ and 1% butanol. The solution was then loaded onto a Sepharose S-column (1.5 cm×10 cm) which was equilibrated with buffer B+1% butanol and 50 mM NaCl. The bound material was eluated by creating a linear gradient up to 500 mM NaCl in the same buffer. Fractions which displayed peak enzyme activity were collected and concentrated to 2.0 ml in Centriprep™ concentrator tubes (Amicon; mwco: 30 kd).

d. Superdex 200 Gel Filtration Chromatography

Gel filtration on Superdex 200 was performed in the same manner as for NAs purification (except that the butanol concentration was 1%) Pure pNA was stored at −20° C. in 50% glycerol.

7. NA Enzymatic Assay

The assay of the catalytic activity of NA was based on the method of Potier et al. (1979). In short, enzyme tests were carried out in a 100 μl reaction volume with 200 mM NaAc pH 6.5, 2 mM $CaCl_2$ and 1% butanol in the presence of 1 mM 2'-(4-methylumbelliferyl)-α-D-N-acetyl-neuraminic acid as substrate. After incubation at 37° C. for 30 to 60 minutes the reaction was stopped by adding 0.5 ml 133 mM glycine, 83 mM $NaHCO_3$, 60 mM NaCl pH 10.7. Free 4-methylumbelliferon was measured by reading the absorption at 365 nm. One unit was defined as that quantity of enzyme which released one nmol 4-methylumbelliferon per minute.

8. Immunologic Techniques a. Preparation of Polyclonal Anti-pNA IgG

A polyclonal antiserum against purified pNA was generated in a three month-old rabbit of the New Zealand strain. The primary immunisation was administered intramuscularly in each paw as four 500 μl doses containing 50 μg pNA/dose and 75% Freund's complete adjuvant. Six weeks later the animal received two corresponding booster injections in both rear paws. For preparation of igG fractions the collected serum was purified by adsorption on protein A Sepharose (Pharmacia LKB).

b. ELISA

Wells of a microtitre plate were coated with anti-pNA IgG of the rabbit. The samples for testing were diluted in PBS with 0.1% bovine serum albumin. Bound antigen was detected with biotinylated anti-pNA IgG of the rabbit followed by streptavidine-alkaline phosphatase conjugate (Boehringer). The enzyme reaction was developed by incubating the plates with p-nitrophenylphosphate (Sigma Chemical Co.). Absorption values were measured at 405 nm in a microtitre plate reader.

9. Analytical Methods

SDS/PAGE was performed according to the Laemmli method (1970) on a 10% separating gel (except where stated otherwise). All samples were denatured in the presence of β-mercaptoethanol, except where otherwise stated. Used as marker proteins in 10% gels were phosphorylase b (94 kd), bovine serum albumin (67 kd), ovalbumin (43 kd), carbonic anhydrase (29 kd) and trypsin inhibitor (20.1 kd, not always visible) (Pharmacia LKB). Gradient gels were run with the following mass standards: myosin (22 kd), β-galactosidase (116 kd), phosphorylase b, bovine serum albumin and ovalbumin (from BioRad). A silver staining was performed on the gels by a modification of the method described by Morrisey (1981). The protein concentration was determined by the method of Bradford (1976) with ovalbumin of the chicken as standard.

10. Cross-linking Analysis

The cross-linking molecule $BS^3$ was freshly prepared as a 1.0 M solution in 10 mM Hepes, pH 7.4. The proteins were cross-linked by adding $BS^3$ to a concentration of 0.5 mM in a reaction volume of 30 μl. The incubation was performed for 1 hour at room temperature. The reaction was subsequently stopped with 5 μl 1.0 M Tris, pH 8.0. Polypeptide patterns were analysed by means of SDS/PAGE.

11. Carbohydrate Analysis

Protein samples (between 0.1 μg and 1 μg) were denatured by boiling in 500 mM Tris/HCl pH 8.0, 0.5% SDS, 50 mM β-mercaptoethanol. After addition of NA-octylglucoside to a concentration of 2.5% resulting in at least a sevenfold excess over the final SDS concentration, NA-glycanase was added (about 0.5 units; units according to the manufacturer) and the reaction mixture was incubated for 16 hours at 37° C. The digestion patterns were analysed on SDS/PAGE.

Results

1. Purification of pNA

In a typical experiment reported here a total of 186 infected eggs were processed. The different purification steps are summarised in table 1. After harvesting of the yolk bag fluid and precipitation of the virus, pronase was added to a concentration of 2 mg/ml and the mixture was incubated for 16 hours at 20° C. After ultracentrifugation roughly 60% NA activity was encountered in the supernatant fraction. It was found that under the said conditions the loss of activity was mainly attributable to an incomplete removal of NA heads of virus particles. Higher pronase concentrations, longer incubation times or increased temperatures did not increase recovery because NA was gradually degraded more (data not shown). The crude pNA material was subsequently diluted and brought to pH 5.5. It was then placed onto a Sepharose S-cation exchanger. For a maximum yield of pNA all further solutions contained 1% butanol. Most of the protein was not held fast on the Sepharose S-column and after gradient elution only a single peak was recorded at about 400 mM NaCl (not shown). This material consisted of substantially pure pNA since no contaminating bands were observed after SDS/PAGE (FIG. 3A, lane 3). In addition, silver staining showed no difference at all between the Sepharose S-pool and an additional Superdex 200 gel filtration step (FIG. 3A, compare lanes 3 and 4). The last column provided a single, bell-shaped peak at fraction 60 (not shown), which corresponds with a molecular weight of about 210 kd. The successive purification steps are illustrated in FIG. 3A.

On SDS/PAGE monomer pNA was in fact visible as a doublet of two bands, corresponding respectively with approximately 54 kd and approximately 52 kd, wherein the latter was the most frequently occurring, as derived from the relative intensities of the silver staining. In all probability this ambivalence derives from a preferred digestion by pronase at two different sites in the stalk region. Cross-linking with the chemical agent $BS^3$ confirmed that pNA was recovered as an authentic tetrameric protein (FIG. 3B).

2. Construction and Expression of NAs

The NA gene of the influenza NA2 strain A/Victoria/3/75 was separated from its NA terminal membrane anchor and coupled instead to the 5' sequence of the A/Victoria/3/75 HA gene which contains a signal peptide splicing site. The synthesis of a secreted, soluble product was hereby made possible. The resulting chimeric gene consists of an HA signal sequence including the codons for the first 4 terminal amino acids of mature HA, followed immediately by the NA sequence lacking the transmembrane part (anchor) and a part of the stalk region (amino acids 1 to 45). Both DNA sequences lie in the same reading frame while no extra amino acids were introduced. Ligation resulted in only a single amino acid substitution corresponding with position 5 of mature HA protein (FIG. 2). A copy of this chimeric sequence, which now substantially codes for a protein which can be secreted, was integrated behind the polyhedrine promoter of AcNPV baculovirus by making use of pVL941 as transfer vector. After inoculation of Sf9 insect cells NA activity was quickly detected in the medium, which shows that soluble protein is indeed produced.

It can be seen in FIG. 4 that the NAs activity in the medium reached a plateau level at roughly 48 hours after infection. Further incubation was unfavourable because the total protein concentration began to fall dramatically, probably as a result of extensive cell lysis. It was found that the expression appeared to be most extensive when intermediary passage between the parent Sf9 monolayer and the extensive suspension culture remained limited to a minimum (data not shown). Based on diverse purification experiments it was determined that NAs were expressed at levels varying from 6 to 8 mg/l, a reasonably low production capacity, but still comparable with yields reported for other secreted complex glycoproteins produced in this system (Jarvis et al., 1990).

3. Purification of NAs

The TC100 medium was harvested 48 hours after infection, at the moment when the specific enzyme activity of the soluble protein content reached a peak (FIG. 4). The different steps of NAs purification are summarised in table 1. Ammonium sulphate precipitation of the crude medium between 20% and 60% saturation provided a moderate, twofold enrichment and enabled concentration of the material. After extensive dialysis and removal of the insoluble products butanol was added to a concentration of 4%. It was found that addition of butanol had a strongly favourable effect on mass recovery of NAs, particularly at low protein concentrations. It is possible that a determined extent of hydrophobicity of the medium was necessary to avoid the formation of insoluble aggregates. The solution was subsequently fractionated by Sepharose Q-anion exchange chromatography (FIG. 5). The NA activity eluated at the beginning of the salt gradient as a reasonably symmetrical peak. According to an ELISA test the remaining fractions contained no NA-related material. At this stage roughly 97.5% of the starting amount of protein was removed, resulting in an increase in the specific activity by a factor of nearly 20. The pH of the solution was then decreased to 5.5 for loading of an N-(p-aminophenyl)oxamic acid-agarose column. It is known from earlier studies that NA-substituted oxamic acids are strong, reversible inhibitors of influenza NA (Edmond et al., 1966). The use of N-(p-aminophenyl)oxamic acid-agarose as selective absorbent for neuraminidases of influenza or bacteria was first demonstrated by Cuatrecasas and Illiano (1971) and later by Bucher (1977). According to the original procedure neuraminidase was eluated with a buffer with a high pH (100 mM $NaHCO_2$, pH 9.1). In our experience however, these conditions allow of only a partial and slow provision of NAs. But efficient desorption could be achieved by combining an increased pH with a high salt concentration. Prior to elution a considerable quantity of aspecifically bound protein was removed from the column by performing an additional washing step at pH 8.5 in the presence of a low salt concentration. By preferring diethanolamine to $NaHCO_3$ as buffer agent the absorption of 2 mM $CaCl_2$ without precipitation was made possible. It has been repeatedly reported that retention of NA activity is somewhat dependent on $Ca^{++}$ ions (Chong et al., 1966; Dimmock, 1971). Whether this was indeed the case in the present study was not investigated in detail.

In order to remove traces of residual contaminants the eluate was concentrated by ultrafiltration and subjected to Superdex 200 gel filtration (FIG. 6). $A_{280}$ check produced three peaks with unequal absorption which eluated at respectively about 220 kd, about 130 kd and about 54 kd. The immunoreactivity patterns of the eluate measured by means of ELISA were found to be a faithful representation of the $A_{280}$ profile for each of the recorded three peaks, which suggests that all the material was NAs-specific. SDS/PAGE analysis of the peak fractions showed an intense band in the expected region of about 55 kd, although a small decrease in molecular weight was observed with increasing fraction number (FIG. 7A). The 220 kd peak was identified as tetrameric NAs by cross-linking analysis with $BS^3$, while the two peaks with a smaller molecule size were found to be respectively dimeric and monomeric NAs, wherein the latter form was of limited quantitative significance (FIG. 7B). It is thought that due to its rod-like structure dimeric NAs eluates slightly above its actual molecular weight in comparison with tetrameric and monomeric NAs, whereof it is thought they have a rounder form. More worthy of note was that the catalytic activity required a fully assembled tetrameric structure of the NAs. It is possible that tetramer formation induces several local confirmational changes which are essential for the enzymatic activity.

The flow diagram of the purification process is shown in table 2.

4. Properties of NAs

Denaturation by boiling with SDS in the presence of β-mercaptoethanol caused a complete disassociation of NAs into monomer chains with a molecular weight close to 55 kd (FIG. 7A). Tetrameric and dimeric NAs were found to be homogeneously purified judging from the silver staining of SDS/PAGE gels. The monomeric NAs were of slightly lesser quality since several traces of contaminants were visible. When they were denatured in the absence of a reducing agent, tetrameric and dimeric NAs migrated as dimeric chains of approximately 110 kd (not shown). These results indicate that NAs dimers are indeed internally linked by disulphide bridges and can further associate through non-covalent interactions, whereby a tetramer protein is formed which corresponds with the structural organization of natural NA.

It has been repeatedly reported that insect cells generate an NA-glycosylation pattern differing to some extent from those produced by mammal and other higher cells (Hsieh and Robbins, 1984; Butter and Hughes, 1981; Butters et al., 1981; Kuroda et al., 1990). The amount of NA-linked carbohydrate associated with recombinant NAs was therefore investigated in comparison to natural pNA. Representative protein samples were treated with NA glycanase enzyme and subsequently analysed by means of SDS/PAGE (FIG. 9). From the relative displacement of the bands it can be concluded that the total amount of NA-linked carbohydrate associated with NAs was slightly smaller compared to the natural molecule (compare FIGS. 9A and 9B), an observation which corresponds with that done for other glycoproteins which are expressed in this system (Kuroda et al., 1986; Domingo and Trowbridge, 1988; van Drunen Littel et al., 1991). It was further also established that the denatured, enzymatically deglycosylated NAs forms migrate with the same electrophoretic mobility irrespective of their original oligomer structure, which confirms that primary NAs was synthesized as a polypeptide with a uniform chain length (FIG. 9B, compare lanes 3, 5 and 9). The molecular weight of the polypeptide chain treated with NA glycanase was estimated at 47.5 kd, which corresponds with the theoretical mass of 47,717 d as calculated from the predicted amino acid sequence. Interestingly enough, the degree of NA glycosylation appeared to be linked to the capacity to form tetramers, since the bands corresponding with glycosylated dimeric and monomeric NAs moved slightly more rapidly in the gel than the band derived from glycosylated tetrameric NAs (FIG. 9B, lanes 4 and 6 as opposed to lane 2; see also FIG. 7A). It has indeed been suggested that NA-linked carbohydrate, more particularly the oligosaccharide chain which is linked to $Asn_{200}$, could play a part in stabilising the tetramer structure by entering into an interaction with a adjoining sub-unit (Varghese et al., 1983; Varghese and Colman, 1991).

Only the tetrameric protein contributed to the catalytic properties of NAs. Isolated tetrameric NAs exhibited a specific level of activity almost identical to that of purified pNA (Tables 1 and 2). The observation that NAs forms of a lower structural order are enzyumatically inactive, even though each monomer has a catalytic cavity, possibly reflects a crucial role for quaternary interactions in the functionality of influenza NA.

In order to verify the antigenic properties of NAs, protein samples of equal concentrations were twice diluted serially and tested in a sandwich ELISA based on polyclonal anti-pNA IgG (FIG. 10). Tetrameric NAs gave a titration curve running identically to the pNA reference graph, which indicates that both have identical or very similar antigenic properties. Despite the absence of demonstrable enzymatic activity, the antigenic activity of dimeric and monomeric NAs remained substantially intact, although a small shift in antigenicity can be observed. This small difference in antigenicity was likewise apparent from the gel filtration profile (FIG. 6) where the antigenic activity/$A_{280}$ ratio of the tetrameric peak was slightly superior. It is possible that a number of antibody molecules generated against the native tetrameric structure were not capable of binding efficiently to incompletely assembled NAs, for instance those which recognise contact areas between adjoining sub-units. Local conformational changes induced by tetramer formation could also cause a number of subtle antigenic differences.

Discussion

The main objective of the present invention was the synthesis of influenza neuraminidase antigen as a secreted, correctly folded protein, together with determining of a purification procedure in order to obtain a homogeneous product which can be used as an agent for vaccination. From the NA gene of the NA2 influenza strain A/Victoria/3/75 was constructed a chimera gene wherein the original NA terminal region which has a combined signal sequence-membrane anchor function, was replaced by the 5' sequence part of an influenza HA gene. The resulting construct which, due to the cleavable signal peptide derived from HA, substantially coded for a secretable NA (NAs), was subsequently incorporated into a baculovirus expression vector under the transcription regulation of a powerful polyhedrine promoter. After infection of Sf9 insect host cells NAs was indeed secreted in the culture medium. Based on the purification results the level of expression was estimated in the range of 6 to 8 mg/l. It was demonstrated that in the course of baculovirus infection the capacity of the host cell to process proteins by way of secretion decreases dramatically (Jarvis and Summers, 1989). The production system as described is nevertheless applicable for laboratory-scale vaccination studies and is suitable for a considerable scaling-up.

The purification of NAs consisted substantially of a four-step procedure comprising a first ammonium sulphate fractionation, followed by a succession of three chromatographic steps. Of the enzymatic activity yields it is estimated that roughly 25% of the NAs was recovered as a purified protein. Through chromatography an a gel filtration column the NAs was sub-fractionated into three populations of different molecule sizes which were identified by cross-linking analysis as respectively tetrameric, dimeric and monomeric NAs, wherein the latter form was present in only very small quantities. The two main forms, tetrameric and dimeric NAs, were obtained in about equal quantities and were homogeneous, judging from SDS/PAGE followed by silver staining.

In order to evaluate the enzymatic and immunologic properties of NAs it was necessary to isolate natural NA as reference protein. A/Victoria/3/75 NA heads of X-47 virus were cleaved by pronase treatment and then purified by cation exchange and gel filtration chromatography. After cross-linking it was confirmed that pNA had retained the tetrameric structure of intact membrane-bound NA.

The catalytic properties of NAs were quite striking since only the tetrameric protein exhibited enzymatic activity. Tetrameric NAs had a specific activity almost equal to that of pNA. It is improbable that dimeric and monomeric MAs were simply inactive because they were denatured proteins, since during the purification procedure these forms were also held fast by affinity chromatography based on the substrate binding site, which suggests that the enzymatic cavity must be functionally intact, but the following catalytic transition can apparently not occur.

Treatment with NA glycanase revealed that on the whole the carbohydrate content of NAs was slightly reduced relative to pNA, a property also observed for other glycoproteins expressed in this system (Kuroda et al., 1986; Domingo and Trowbridge, 1988; van Drunen Littel et al., 1991). Hypoglycosylation was apparently more pronounced for dimeric and monomeric NAs.

Structural studies by X-ray diffraction analysis indicated that the carbohydrate chain linked to $Asn_{200}$ makes close contact with an adjoining sub-unit, which suggests that it could provide additional interactions to strengthen the quaternary structure (Varghese et al., 1983; Varghese and Colman, 1991).

The reactivity of tetrameric NAs with polyclonal IgG generated against purified pNA was substantially complete, which indicates that both proteins have very similar antigenic properties. It was possible to observe a small shift in antigenicity in the case of dimeric and monomeric NAs. It could be inferred herefrom that it should be possible to isolate monoclonal antibodies which only bind on the tetrameric structure of influenza NA. Such an antibody would probably enter into an interaction with surface determinants derived from adjoining sub-units or, in the alternative case, it could recognise epitopes formed after conformational rearrangement during tetramer formation. In addition, differences in carbohydrate composition could also modulate the antigenic properties.

EXAMPLE 2

Secretion of Recombinant Neuraminidase by *Pichia Pastoris*

Introduction

In order to investigate whether a yeast could be used as host cell in addition to insect cells for the production of recombinant influenza neuraminidase, an expression vector was constructed which contained the enzymatic "hat" part of the neuraminidase.

Materials and Method

1. Vector and Host

The *Pichia pastoris* plasmide pPIC9 (Invitrogen) was used to construct the expression cassette. This plasmide comprises a replication origin, an ampicillin resistance gene, the promoter and terminator regions of the inducable alcohol oxidase I (AOXI) gene of *P. pastoris*, the prepro secretion signal of the α-factor of *Saccharomyces cerevisiae* and the HIS4 marker of *P. pastoris*.

The methylotrophic yeast *Pichia pastoris* (Invitrogen) was used as host.

2. Construction of the Expression Cassette

By means of site-oriented mutagenesis a StuI restriction site was introduced into the cDNA sequence of the neuraminidase gene of A/Victoria/3/75. The restriction site was situated at the position of Pro79. Using this restriction site the immunogenic "hat sequence" of the neuraminidase gene containing the enzymatically active centre could be isolated as a StuI/HindIII fragment and cloned in the SnaBI restriction site of the *P. pastoris* plasmide pPIC9. FIG. 15 shows a diagram of the pPIC9 plasmide. FIG. 16 is a view of the fusion region between the prepro signal sequence and the recombinant neuraminidase. The propeptide is cleaved in the late Golgi via the endogenous KEX2 protease. The $(Glu-Ala)_2$ dipeptide is removed by an STE13-type dipeptidyl amino-peptidase. The extra tyrosine residue is not cleaved and remains present N-terminally on the recombinant neuraminidase, but is not required.

The resulting plasmide was linearised at the position of the HIS4 selection marker by means of a SalI digest and subsequently transformed into *P. pastoris* GTS115 (his4) protoplasts in the presence of polyethylene glycol. DNA isolated from the transformants was subjected to a Southern analysis. This showed that the expression vector integrated via homologous recombination at the position of the internal (but deficient) his4-locus. Most transformants possess 1 to 2 copies of the plasmide but transformants with a higher secretion capacity were found to possess multiple copies which were integrated head to tail in the host genome in a tandem structure. The number of copies rose to 25 per transformant.

3. Expression of the Neuraminidase

Transformants were pre-grown in buffered minimal glycerol medium (pH 6.0) and transferred after 48 hours to buffered minimal medium containing 0.5% methanol. The alcohol oxidase I promoter was hereby induced and the neuraminidase "hat" expressed. Using a per se known Northern analysis an estimate was made of the quantity of mRNA of the neuraminidase in the cell. This showed that a very efficient induction took place.

A Western analysis of the cell supernatant showed that the recombinant neuraminidase with a molecular weight of approximately 78 kDa was secreted therein (see FIG. 17).

The secreted product was deglycosylated with PNGase F. This produced a "core" product with the expected size of 43 kDa. Depending on the number of copies the yield of recombinant neuraminidase in the medium was found to fluctuate between 1 and 1.5 mg/l.

EXAMPLE 3

Immunisation

Materials and Methods

1. Animals

Female inbred Balb/c mice (SCK Mol, Belgium) were 8 weeks old at the beginning of the immunisation procedure. In passive immunisation experiments recipient mice were 12 weeks old. The mice were accommodated in groups of three animals per cage (410 $cm^2$) and had access to food and water ad libidum.

2. Viruses

Influenza strains were made available by Dr. A Douglas and Dr. J. Skehel (MCR Laboratories, Mill Hill, London). The laboratory viruses X-31 and X-47 have an H3N2-antigen composition and are derived through genetic rearrangement from A/PR/8/34 (H1N1) with respectively A/Aichi/2/68 (H3N2) and A/Victoria/3/75 (H3N2). Both virus stocks were adapted by a number of passages through lungs such that they caused death in mice.

3. Recombinant Secretable NA (NAs)

Influenza NA A/Victoria/3/75 was administered as a purified recombinant protein produced by a baculovirus insect cell expression system, as described in Example 1. The purified NAs preparation that was used for the immunisation experiments described herein contained a mixture of tetrameric and dimeric molecules in phosphate-buffered salt solution (PBS).

4. Adjuvants

Suitable adjuvants were chosen on the basis of an immunization study with recombinant influenza HA which was performed in our own laboratory. Ribi-adjuvant (with monophosphoryllipid A (MPLA)), trehalose-6,6-dimycolate (TDM), squalene and Tween 80) and *Salmonella typhimurium* MPLA bottles were filled in accordance with the instructions of the manufacturer (Ribi Immunochem Research). Muramyl dipeptide (MDP) was purchased from Sigma Chemical Co..

5. Immunisation Protocol

The mice were injected subcutaneously at three-weekly intervals with three 200 μl-doses of 1 μg NAs each. For the first immunization NAs was emulsified in half the amount of a normal Ribi mouse dose (corresponding with 25 μg MPLA, 25 μg TDM, 2 μl squalene and 0.1% Tween 80). Booster injections were given by adding 25 μg MPLA and 25 μg MDP to NAs. The control animals received adjuvant dissolved in PBS.

6. Passive Immunisation

Three weeks after receiving a third immunisation blood was taken from the donor mice by heart puncture and serum preparations of correspondingly treated mice were pooled. Recipient mice received a single intraperitoneal injection of 400 μl immune or control serum.

7. Influenza Challenge

Under a light ether anaesthetic the mice were inoculated intranasally with 20 $LD_{50}$ of the specified virus three weeks after the last booster injection or one day after passive immunisation. The progress of the infection was then followed by measuring the rectal temperature and the body weight for a post-inoculation period of 10 days.

8. Serological Method

One day before the start of the vaccination procedure (pre-immune serum) and two weeks after each immunisation blood samples were taken from the tail artery. Individual serum samples were tested for NA-specific antibodies by means of ELISA. Microtitre plates (Nunc Maxisorp) were coated with purified NAs (50 ng/well) and the sera were diluted in a 1/5 series. Binding of specific antibody was quantified by adding anti-(mouse IgG) antibody of the rabbit conjugated with alkaline phosphatase (Sigma Chemical Co.), followed by incubation of the plates with p-nitrophenol substrate solution (Sigma Chemical Co.). The OD-values were measured at 405 nm in a microtitre plate reader. The titre of NA-antibody was expressed as the reciprocal of the $\log_5$-serum dilution resulting in an absorption of 0.05 higher than the control wells (treated with pre-immune serum).

Results

1. Study Design

Three groups of 12 mice were vaccinated with NAs in accordance with the above described immunisation protocol. An equal number of control mice was treated in parallel with PBS. Paired groups of vaccinated and control mice were subsequently challenged with mouse-adapted X-47 or X-31. In the alternative case they served as serum donors for passive immunisation experiments.

2. Serological Responses

The antibody response against NAs was followed by ELISA in the serum of a random selection of 12 vaccinated and 12 control animals (1 animal from each cage) (FIG. 11). The use of the NAs immunization procedure in mice caused a steady increase of NAs antibodies in the serum. The first booster injection caused an increase in NAs antibodies of approximately three $\log_5$ quantities, while a second booster injection resulted in yet another approximately five-fold increase in the NAs antibody titre. In control mice the single administering of adjuvant did not result in a significant production of aspecific antibodies which reacted with NAs.

3. Homovariant Protection with NAs

Three weeks after vaccination vaccinated and control mice were examined for immunity by administering 20 $LD_{50}$ of the homo-NA-variant virus X-47 (FIG. 12). All control mice became seriously ill, as determined by measuring an increasing fall in the body temperature and loss of body weight. On day 4 after infection the first victims were counted and all controls were dead within 9 days of inoculation. In contrast the clinical parameters in the NAs vaccinees fell only transitorily and to very modest extent. All vaccinated animals survived the infection.

Also investigated was whether the same level of protective immunity could be achieved without a third immunization, possibly via compensation by higher doses of NAs and/or adjuvant. These tests had substantially the same experimental design. Although mice immunised in this manner generally displayed a good resistance, a few individual cases became seriously ill and a number of the vaccinees occasionally died, although the survival percentage was seldom lower than 80%. But the level of protective immunity achieved by three immunisations was found to be superior all along the line.

4. Heterovariant Protection with NAs

Parallel groups of vaccinated and control mice were examined for immunity with 20 $LD_{50}$ of the hetero-NA-variant virus X-31 which has an NA which is separated from the NAs derived from A/Victoria/3/75 by 7 years of antigen drift (FIG. 13). As also observed for the X-47 immunisation study, the clinical consequences of infection in the control group were dramatic. Control animals already began to die 5 days after infection. Mortality reached a maximum on day 6, whereafter only one survivor remained. Mice immunised with NAs displayed 100% survival after the normally lethal heterovariant infection. Just as in the homovariant immunity study the vaccinees were here also capable of maintaining their body temperature at reasonably normal levels. The loss of body weight was somewhat more pronounced but all mice began to recover from day 6.

5. Protective Immunity can be Obtained by Passive Transfer of NAs Immune Serum

In order to determine whether it was the humoral defence mechanisms which were mainly responsible for causing protective immunity, the protection of animals by passive immunisation was tested. For this purpose donor mice were immunised according to the standard procedure. Removal of blood from the animals provided an average of about 400 μl serum per individual. After pooling on the one hand of control sera and on the other of immune sera recipient mice were injected intraperitoneally with a single dose of 400 μl serum. Prior to the challenge with 20 $LD_{50}$ adapted X-47 virus a period of 24 hours was interpolated to enable systematic spreading of the antibody molecules in the mice. While animals which had received control serum subsequently developed acute hypothermia and suffered serious weight loss ultimately leading to death, administering of NAs immune serum protected the mice to substantially the same extent as was demonstrated for the actively immunised animals (FIG. 14). It can therefore be concluded that pre-circulating NA antibodies are capable of and sufficient for providing complete protection.

Discussion

The immunity to influenza was studied for a long time almost exclusively as a function of HA antibody, while the importance of NA in contributing to immunity was substantially ignored. This situation resulted partly from the observation that only antibodies capable of binding HA had the capacity to directly neutralise virus particles (Hirst, 1942; Davenport et al., 1964; Kida et al., 1983), while antibodies against NA did not appear to be capable of preventing a primary infection over a great range of concentrations (Jahiel and Kilbourne, 1966; Kilbourne et al., 1968; Johansson, 1989). This tolerance probably reflects the late part NAs played in the life-cycle of an influenza virus by preventing newly formed virus from aggregating at the surface of the infected cell (Colman and Ward, 1985; Brown and Laver, 1968). It was moreover found that NA, in contrast to HA, was the lesser component of the influenza envelope, a fact which could further contribute to the non-neutralising effect of NA antibodies (Schulman et al., 1968). This difference in molar presence likewise affects the relative antibody responses to the individual antigens. Repeated over-presentation of HA relative to NA due to successive confrontations with the whole influenza virus could result in suppression of the NA antibody production, probably as a consequence of the weakened help of Na-specific T-cells (Kilbourne, 1976; Johansson et al., 1987; Kilbourne et al., 1987; Johansson et al., 1987). In order to study the protective NA immunity it is therefore necessary to develop systems in which the interference of neutralising HA antibodies is eliminated and inhibition of the NA immune response through competition of HA and NA antigens is avoided. Classical approaches were either based on the isolation of the natural NA component (Schulman et al., 1968; Johansson and Kilbourne, 1990; Gallagher et al., 1984) or were based in the alternative case on the combined administration of a defined series of influenza strains with serologically differing HA and NA antigens (Rott et al., 1974; Kilbourne, 1976). The results described here directly demonstrate however a protective immunisation by means of a purified, recombinant NA protein. The NA-gene of A/Victoria/3/75 (H3N2) virus was transformed to a gene which codes for a secretable protein (NAs) through replacement of the region that codes for the membrane anchor by the signal sequence of an influenza hemagglutinin gene (see example 1).

In vitro techniques have already established that NA antibodies can efficiently suppress the yield of virus growth by inhibiting the release and spread of virus particles (Jahiel and Kilbourne, 1968; Kilbourne et al., 1968). Similar conclusions were drawn from animals immunised with NA by measuring decreased virus titres in the lungs and reduced development of lung lesions (11,12,13). Although considerable attention has been devoted to the effect of the NA immunity on virus replication in the lungs, it was questionable whether immunisation with pure NA protein could prevent clinical disease symptoms or could improve the chances of survival after a potentially lethal influenza infection. No satisfactory answer has as yet been provided to this question. The results shown here clearly demonstrate however that complete protection against a normally lethal influenza infection can be achieved by immunisation with pure recombinant NAs, wherein any possible contribution from anamnestic anti-HA immune mechanisms or cell-mediated memory immune effects against antigens of conserved internal viral proteins is excluded.

In the experiments presented here, mice were immunised with three doses of 1 μg NAs which were given in intervals of three weeks. Vaccinated animals were capable of totally surviving a lethal infection of influenza virus, wherein the virus expressed homo- or heterovariant NA. In view of the high dose of infection virus it was very striking how well immunised animals remained free of clinical disease symptoms as indicated by changes in temperature and body weight. It is important to note that the adjuvants which were administered together with NAs all have low reactogenic properties, so that the immunisation procedure described herein is directly applicable for human vaccination. The vaccines according to the invention are in addition relevant for other mammals and for birds.

Passive transfer of serum of mice which were immunised with NAs to naive recipient mice resulted in the same levels of protection, which indicates that the protective effect of NAs immunisation can be explained on the basis of circulating NA antibodies.

With regard to the heterovariant protection described herein, it is important to consider the structural relation between the NA antigen of the vaccine A/Victoria/3/75 and the NA of A/Aichi/2/68 which is present in the variant infection virus X-31. Unfortunately, no sequence data is available relating to the NA of A/Aichi/2/68 (H3N2), although a comparison can however be made with the NA sequence of A/NT/60/68 (H3N2) (Bentley and Brownlee, 1982), isolated in the same year as the Aichi strain. Examining closely the head region of both NA variants, amino acid substitutions are found at 28 positions, wherein the majority is located on the surface of the molecule.

It is probable that the vaccine according to the invention can also provide protection against still further removed drift variants. It is further conceivable that by means of genetic modification of the NA gene variations can be arranged in the antigenic structure thereof. It hereby becomes possible for instance to prepare "cocktails" of different versions of the NA, whereby extensive protection against different influenza strains can be obtained.

BRIEF DESCRIPTION OF DRAWINGS

FIG. 2 shows the nucleotide sequence of the positive cDNA string and the amino acid sequence of the flanking regions of the ligation site between the HA signal peptide and the NA with its NA membrane anchor removed.

FIG. 2A shows non-processed HA with, in detail, the signal peptidase restriction site between $Ala_{16}$ and $Gln_1$, (dotted vertical line). The NA terminal segment used for the secretion of NAs is designated with an arrow.

In FIG. 2B is shown a detail of the “stalk” region of NA. The truncated sequence involved in the construction of NAs is designated with an arrow.

In FIG. 2C is shown how the sequence of NAs is constructed from A and B. Shown here in detail is the fusion region between HA- and NA-specific sequences. NAs probably begins with the four NA terminal amino acids of mature HA followed by a mutated codon (underlined with a dotted line).

In FIG. 3 the SDS/PAGE-analyses of purified pNA are shown. FIG. 3A relates to the analysis of protein samples taken in the different steps during purification of pNA. Lane 1 shows the marker proteins; lane 2 the crude pNA material (1 μg; pNA bands below detectable levels), lane 3 shows the Sepharose S-pool (1 μg); lane 4 the Superdex 200-pool (1 μg) . Shown in FIG. 3B is a 5.0% to 7.5% gradient gel of 1 μg pNA cross-linked by means of $BS^3$. Lane 1 shows the marker proteins; lane 2 the pNA after cross-linking. Extra bands appear at about 105 kd (dimer), about 160 kd (trimer) and about 210 kd (tetramer).

FIG. 4 shows the time progression of specific activity (□) which is detected in the culture medium, as derived from the enzymatic activity levels (○) and the total protein concentration (◇), after inoculation of Sf9 cells with recombinant baculovirus.

In FIG. 5 the anion exchange chromatography on Sepharose Q is shown. After dissolving and dialysing the (20–60)% $(NH_4)_2SO_4$ precipitate, the solution (97.5 mg protein, 117,000 U) was loaded onto a Sepharose Q-column. Non-bound material was washed away before the elution was performed with a linear NaCl gradient (---) to a concentration of 250 mM which was added to the starting buffer. The protein concentration of the eluate was followed by $A_{280}$-measurement (___). Fractions of 2.5 ml were collected and tested for enzymatic activity (○) and for antigenicity in an ELISA (Δ).

FIG. 6 shows the gel filtration of NAs on Superdex 200. The eluate after N-(p-aminophenyl) oxamic acid-agarose separation (2.63 mg protein, 49,100 U) was concentrated to 2.0 ml and subsequently chromatographed in fractions of 1.0 ml sample volume on a Superdex 200-column run at a throughflow rate of 10 ml/hour. $A_{280}$ was continuously followed (___). Individual fractions (1.0 ml) were tested for enzymatic (○) as well as antigenic activity (Δ). The arrows indicate the elution volumes of the calibration proteins (see text) 443 kd (1), 200 kd (2), 150 kd (3), 67 kd (4) and 29 kd (5).

FIG. 7 shows the SDS/PAGE analysis of purified NAs. Each lane corresponds with the specified fraction number of the Superdex 200 gel filtration. FIG. 7A shows the SDS/PAGE pattern after denaturation of 10 μl samples (β-mercaptoethanol was added). The lanes A and B indicate marker proteins. In FIG. 7B the protein samples were cross-linked with $BS^3$ and subsequently separated by electrophoresis on a gradient gel of 5.0% to 7.5% in the presence of SDS but under non-reducing conditions. The fractions 57 to 68 show 10 μl sample volume; fractions 70 to 77 show 25 μl sample volume. Tetrameric NAs causes bands at about 220 kd (tetramer) and about 110 kd (dimer). Dimeric and monomeric NAs remain visible as bands of respectively about 110 kd and about 55 kd.

Shown in FIG. 8 are the SDS/PAGE results of protein samples taken during different steps of the NAs purification procedure. Lane 1 shows the marker proteins; lane 2 the crude medium (5 μg); lane 3 (20–60)% $(NH_4)_2SO_4$ precipitate (5 μg); lane 4 the Sepharose Q-pool (2.5 μg)); lane 5 the pool after N-(p-aminophenyl) oxamic acid agarose separation (1 μg); lane 6 the pool of tetrameric and dimeric NAs fractions after Superdex 200 gel filtration (1 μg).

FIG. 9 shows the comparative analysis of the carbohydrate content linked to pNA and NAs, as estimated from NA-glycanase digestion and SDS/PAGE. The enzyme NA-glycanase is visible as a band of about 35 kd. In FIG. 9A lane 1 shows the marker proteins; lane 2 non-digested pNA (1 μg); lane 3 pNA (1 μg) treated with NA-glycanase. In FIG. 9B lanes 1 and 8 show the marker proteins; lane 2 non-digested tetrameric NAs; lane 3 tetrameric NAs treated with NA-glycanase; lane 4 non-digested dimeric NAs; lane 5 dimeric NAs treated with NA-glycanase; lane 6 non-digested monomeric NAs; lane 7 monomeric NAs treated with NA-glycanase.

FIG. 10 illustrates the antigenic near-identicity between NAs and pNA. Samples of pNA and NAs were brought to an equal protein concentration and then serially diluted 1 to 2 in an ELISA. The figure shows the sigmoid antigenicity curve measured for the specific antigens. The pNA reference is indicated by ○; the tetrameric NAs by ◇; the dimeric NAs by □ and the monomeric NAs by Δ.

The antibody response to NAs is illustrated in FIG. 11. Fourteen days after each immunisation (designated by means of an arrow), blood samples were taken from the mice and the presence of NAs antibodies was measured in an ELISA (see text for experimental details). Full-shaded bars and hatched bars represent average serum titres (± S.D) of vaccinated and control animals respectively. FIG. 12 shows the homovariant protection. Vaccinees [___ in (A); ▼ in (B) and (C)] and controls [___ in (A); ● in (B) and (C)] were challenged with 20 $LD_{50}$ of homovariant, mouse-adapted X-47 virus. The progress of the infection was followed by recording the rate of survival (A) and by measuring the rectal temperature (B) and the body weight (C) of the mice (see text for experimental details). The data points give average values ± S.D.

The heterovariant protection is illustrated in FIG. 13. Vaccinees [--- in (A); ▼ in (B) and (C)] and controls [___ in (A); ● in (B) and (C)] were challenged with 20 $LD_{50}$ of heterovariant, mouse-adapted X-31 virus. The progress of the infection was followed by recording the rate of survival (A) and by measuring the rectal temperature (B) and the body weight (C) of the mice (see text for experimental details). The data points give average values ± S.D.

FIG. 14 shows the protection by passive immunisation. Groups of mice were passively immunized by intraperitoneal injection of NAs immune serum. [--- in (A); ▼ in (B) and (C)] or control serum [___ in (A); ● in (B) and (C)]. Twenty-four hours later they received a challenge of 20 $LD_{50}$ mouse-adapted X-47 virus (see text for experimental details). Rate of survival, rectal temperatures and body weight are shown in respectively (A), (B) and (C). Data points indicate the average value ± S.D.

TABLE 1

Purification of pNA

Figure 1:
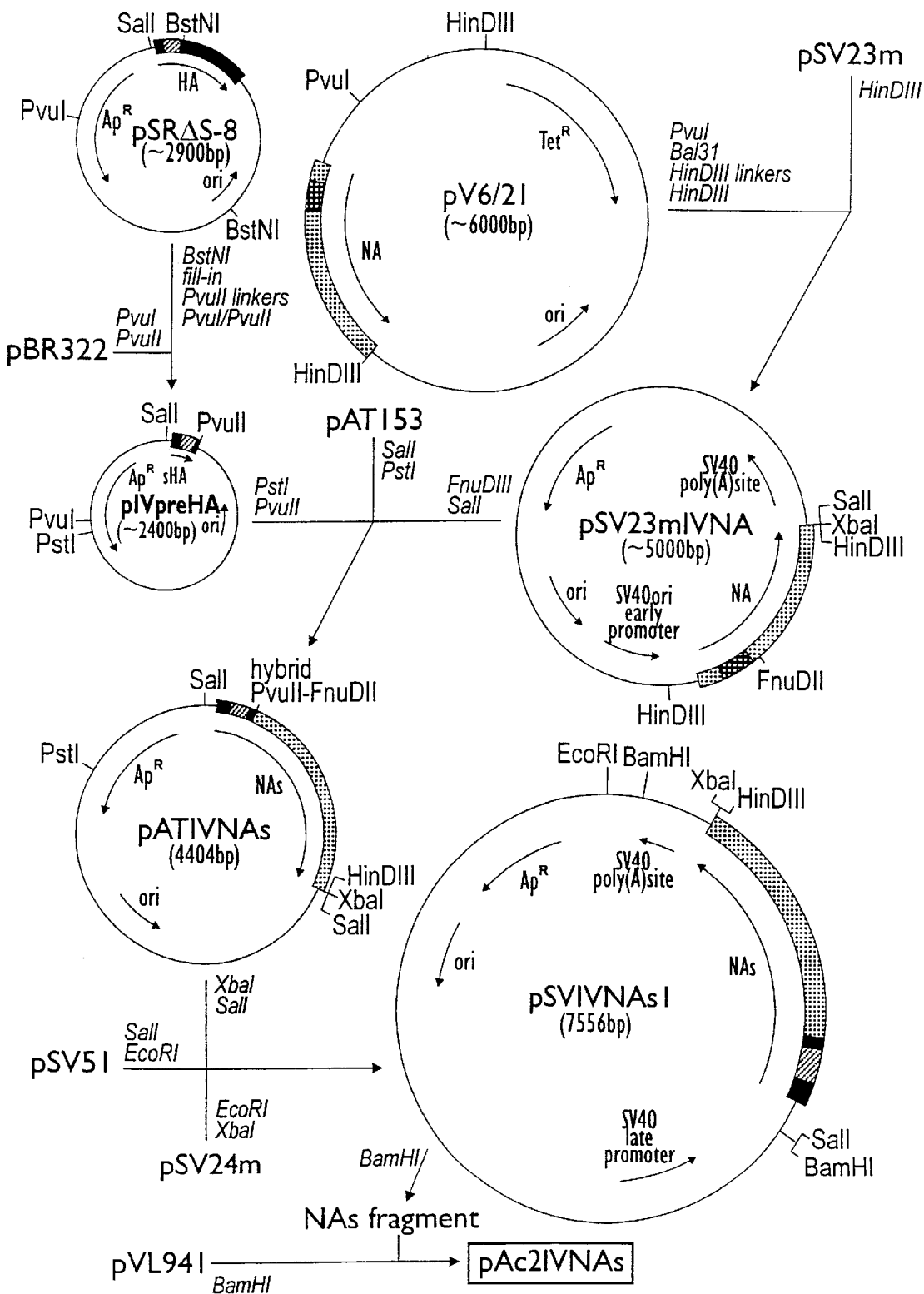
FIG. 1 shows the strategy for the construction of a secretable NA gene and its integration in a baculovirus transfer vector. Only the relevant restriction sites are indicated. The single lines show bacterial plasmide sequences, while the denser portions indicate HA-specific (full) or NA-specific (dotted) sequences. The HA signal sequence is indicated with single hatching. The NA signal sequence/membrane anchor sequence is indicated with double hatching.
Figure 3A:
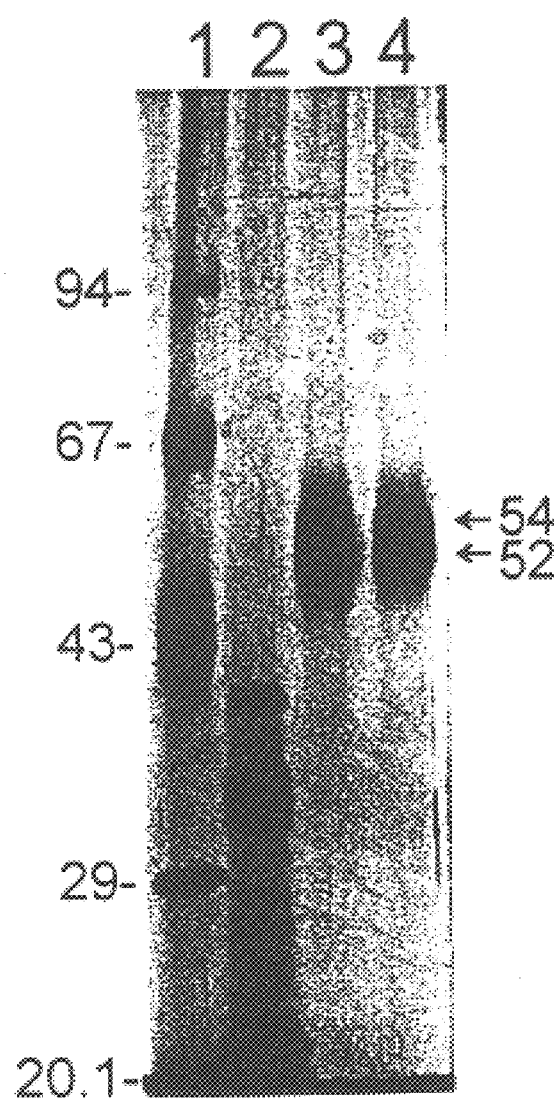
Figure 3B:
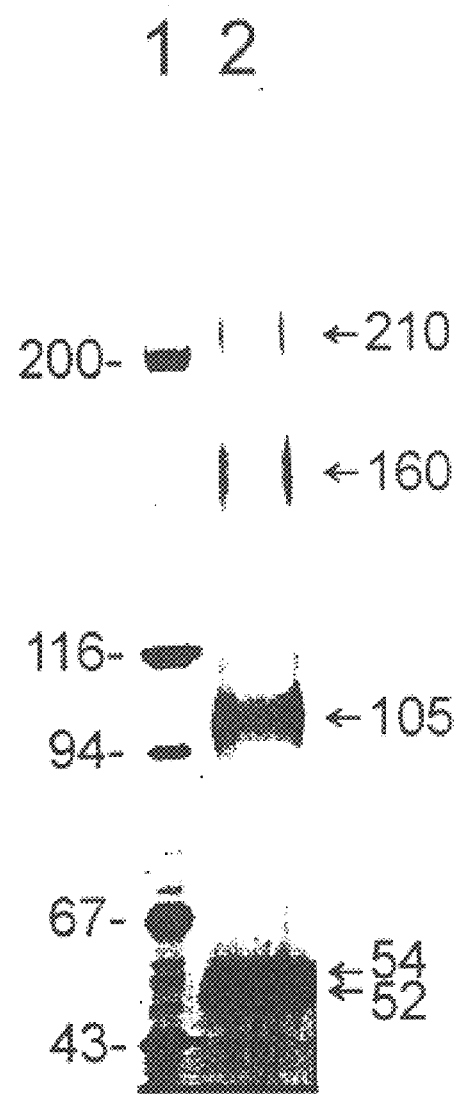
Figure 4:
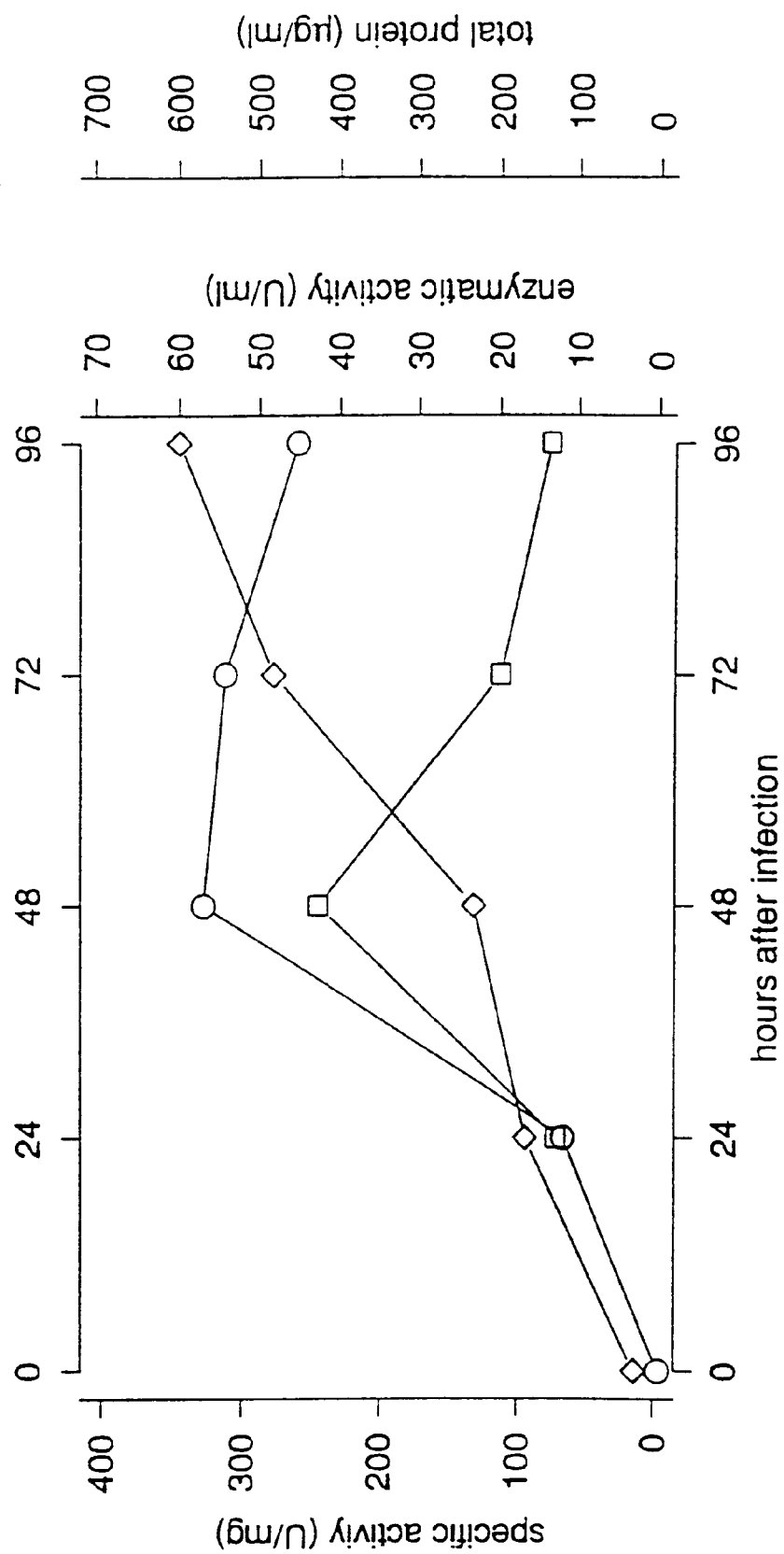
Figure 5:
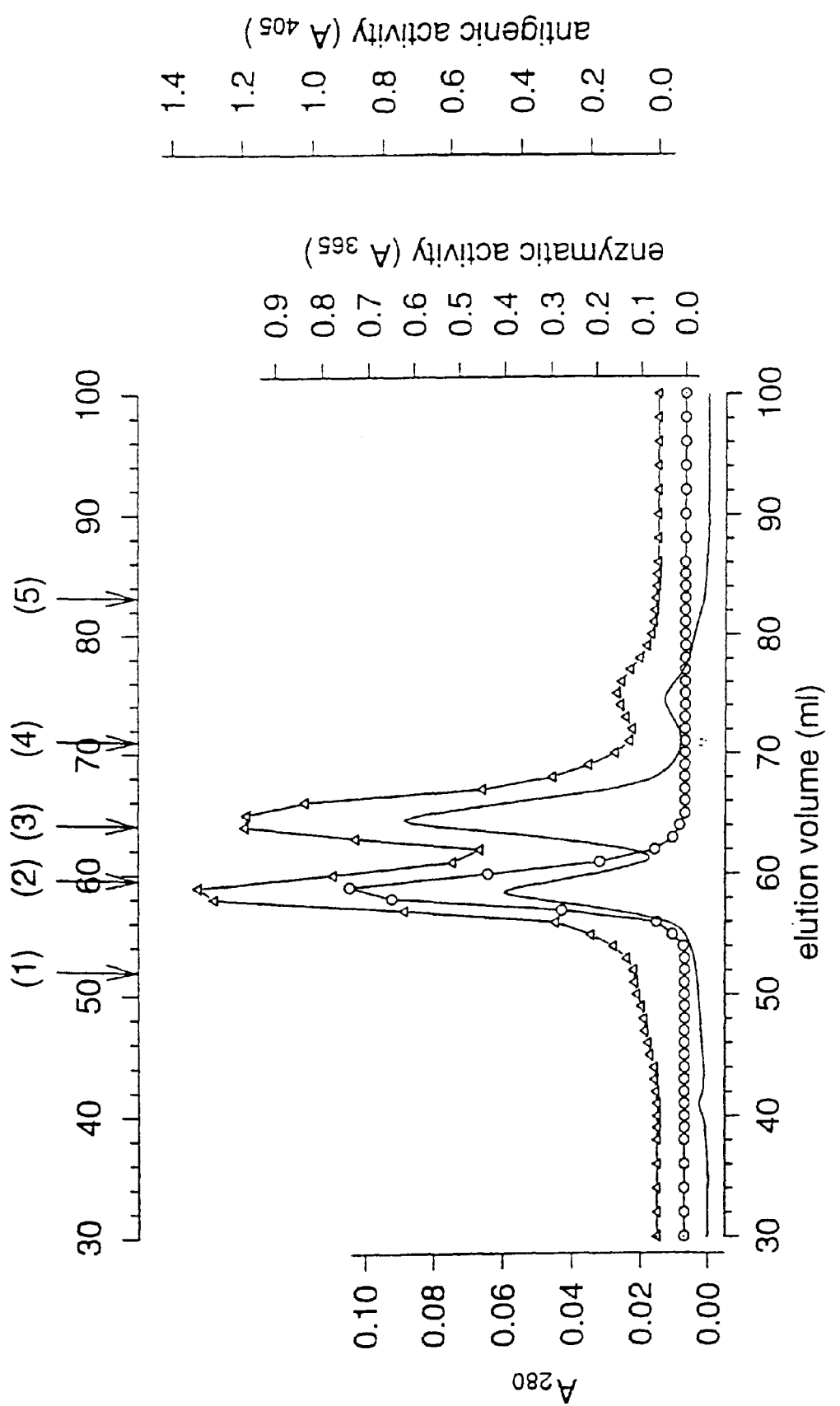
Figure 6:
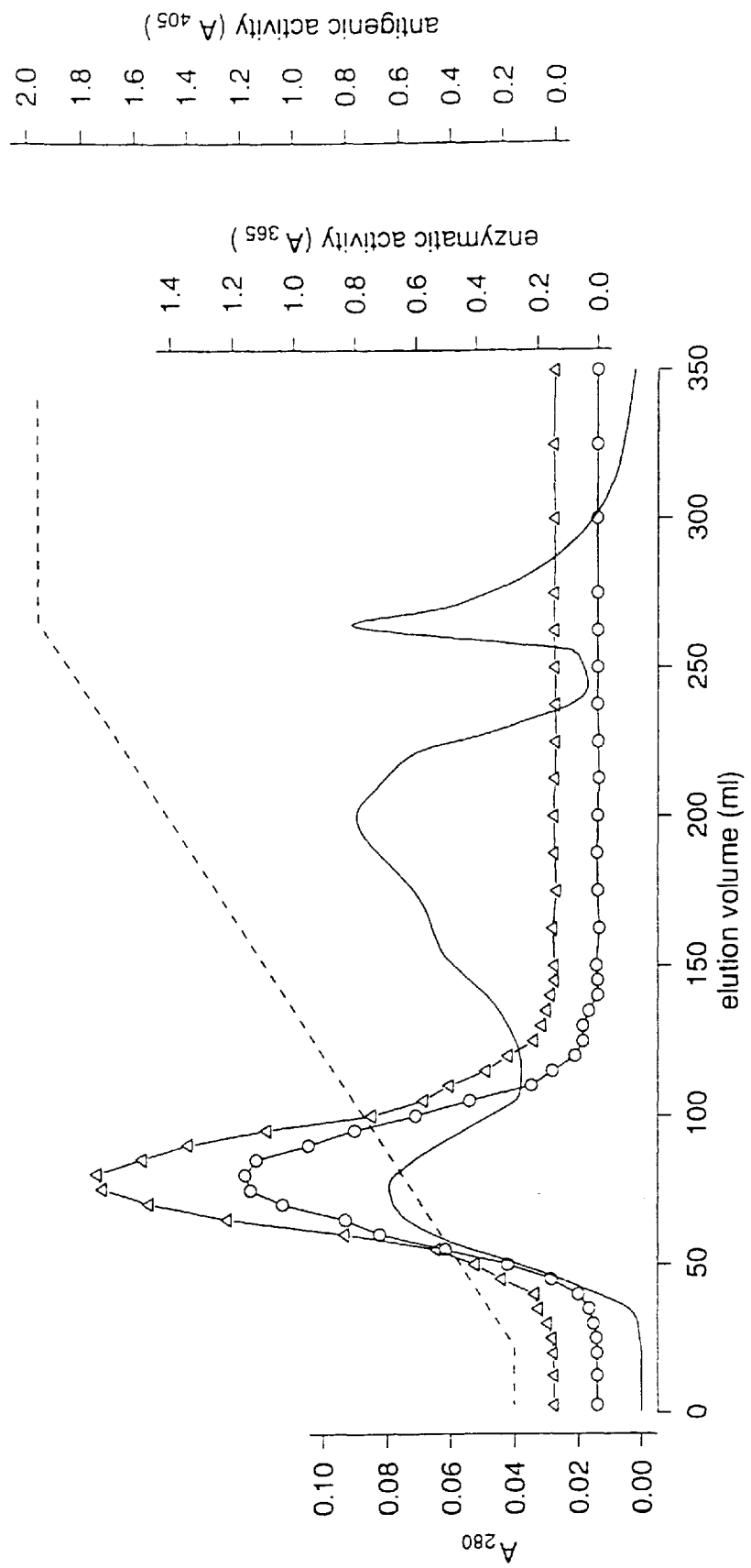
Figure 7A:
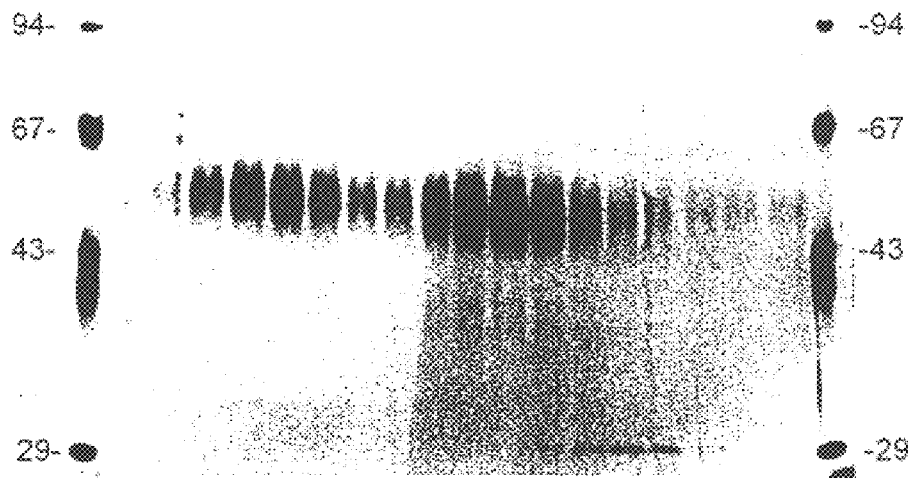
Figure 7B:
Figure 8:
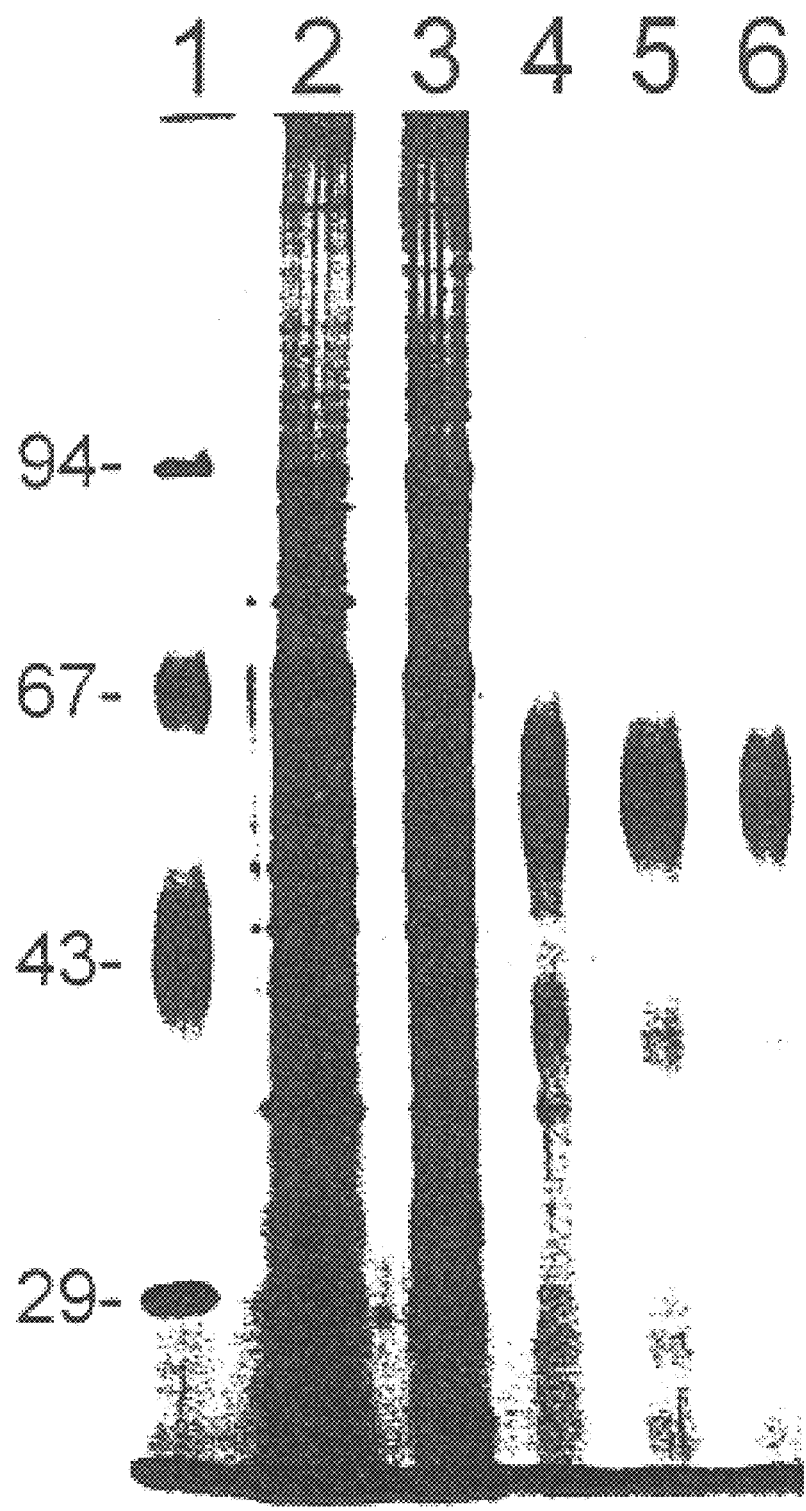
Figure 9A:
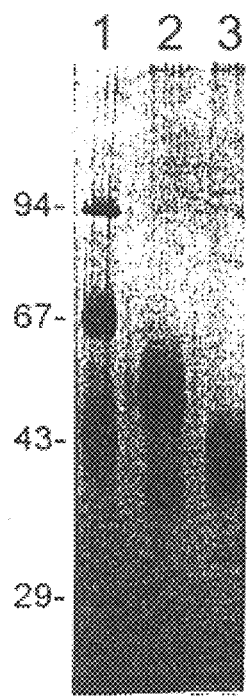
Figure 9B:
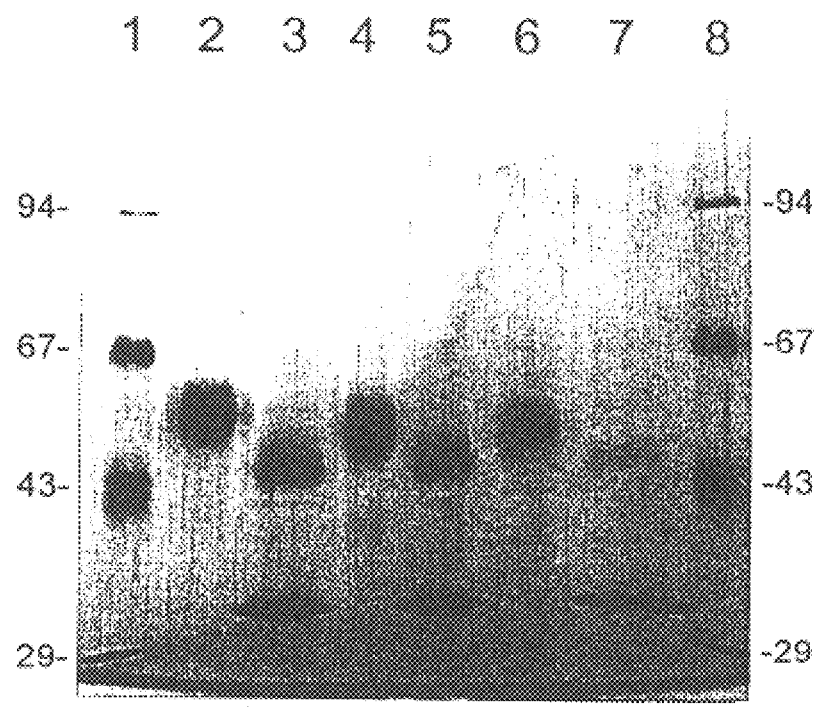
Figure 10:
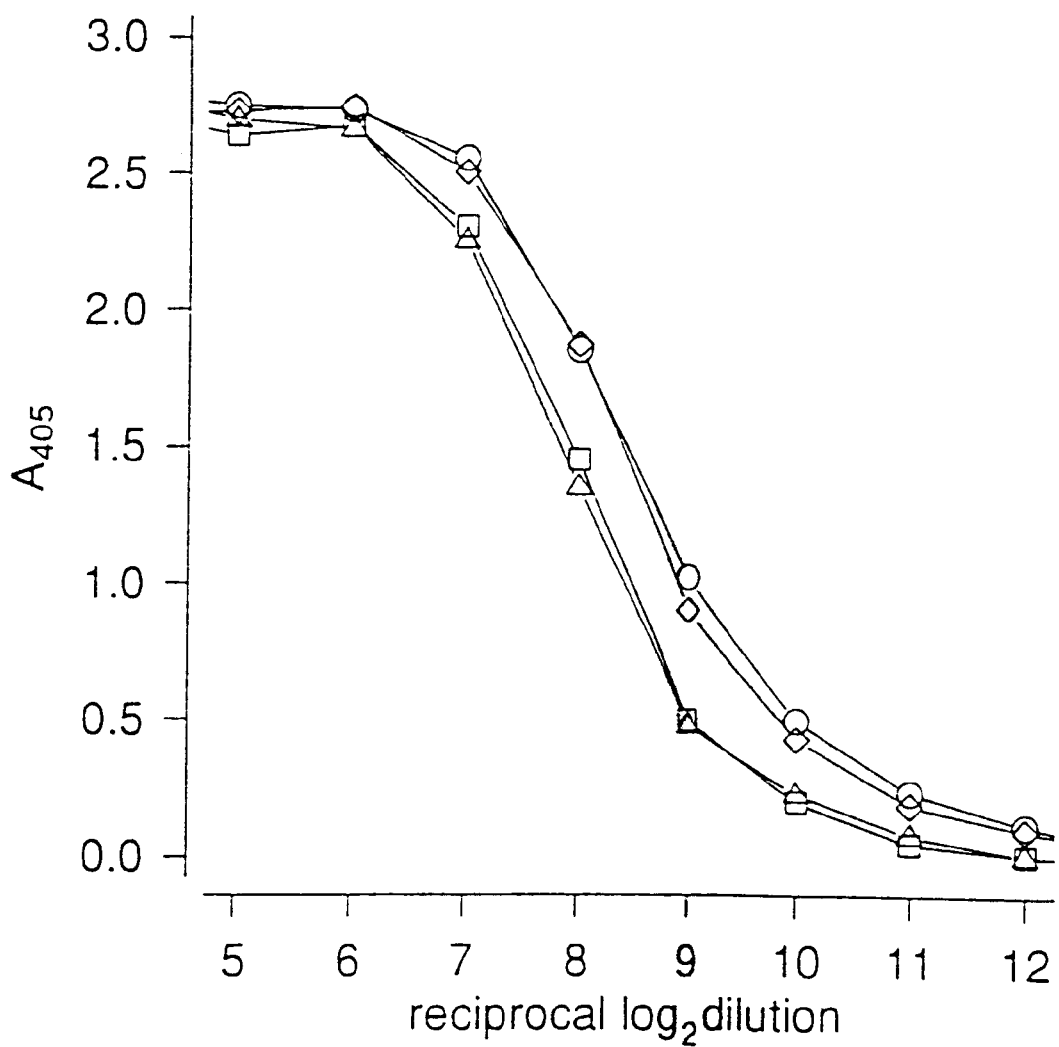
Figure 11:
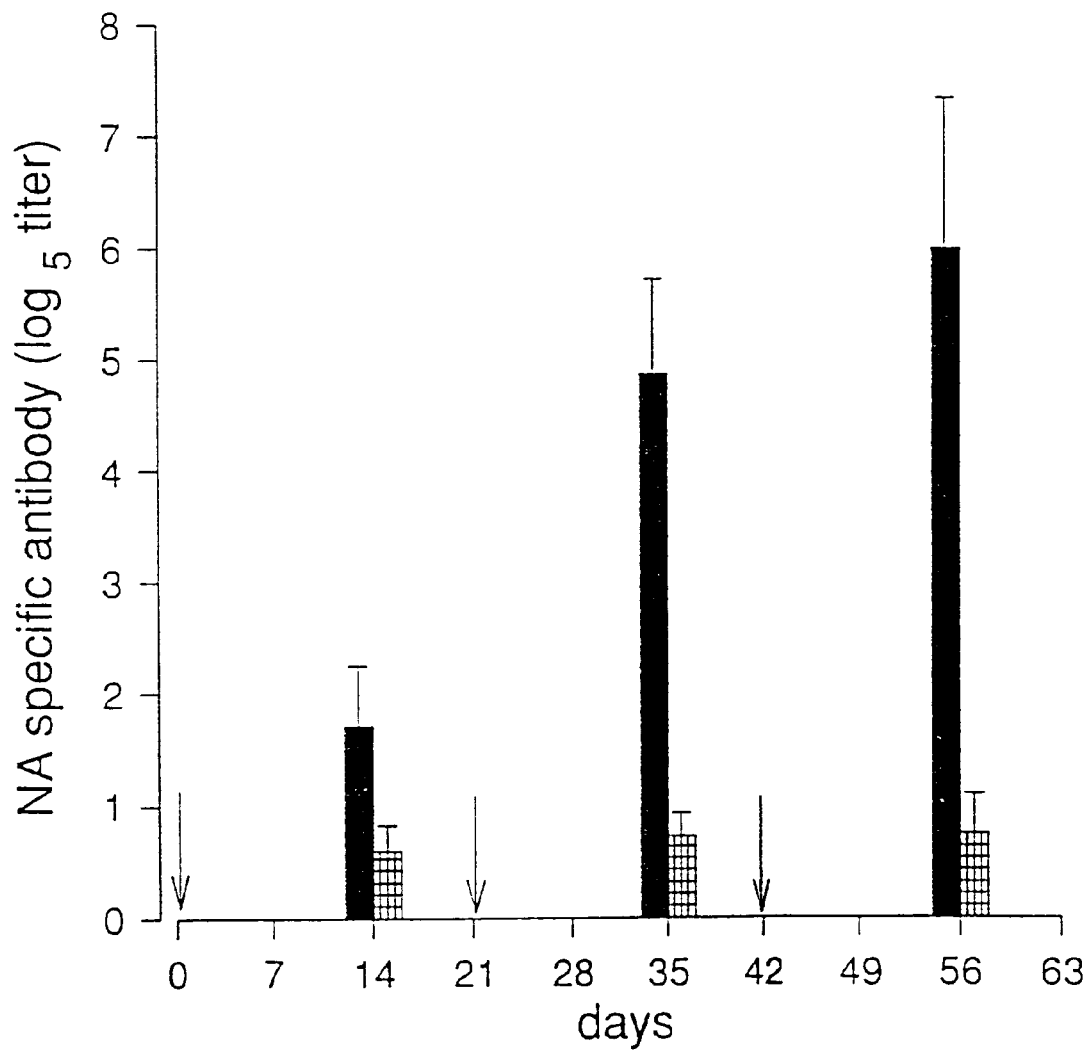
Figure 12A:
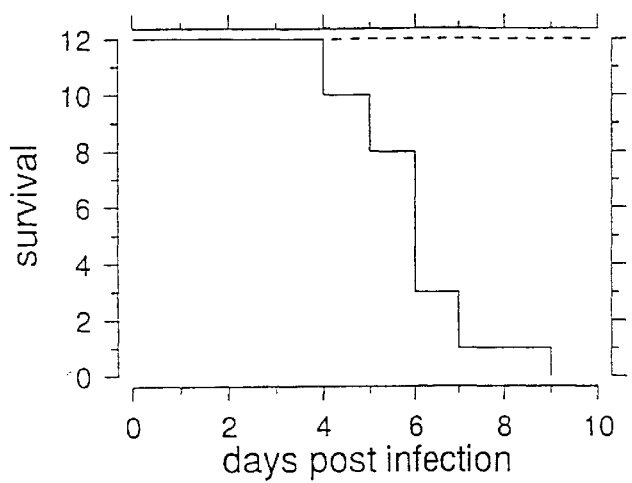
Figure 12B:
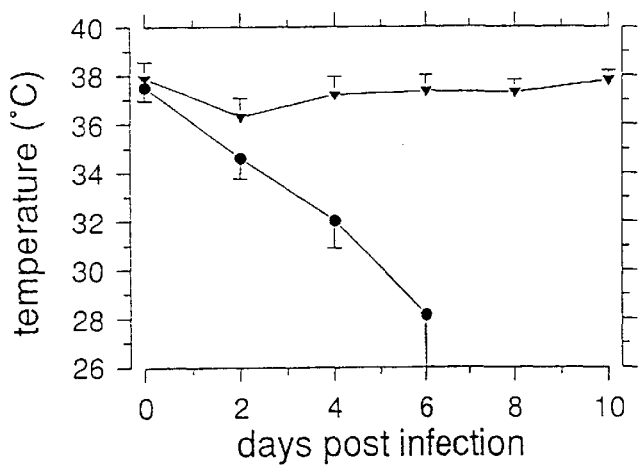
Figure 12C:
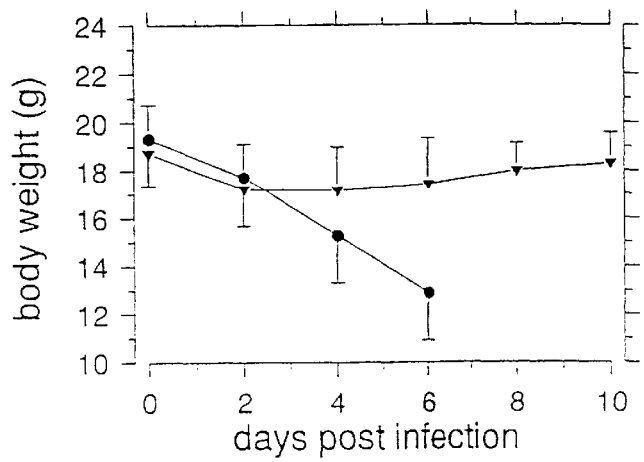
Figure 13A:
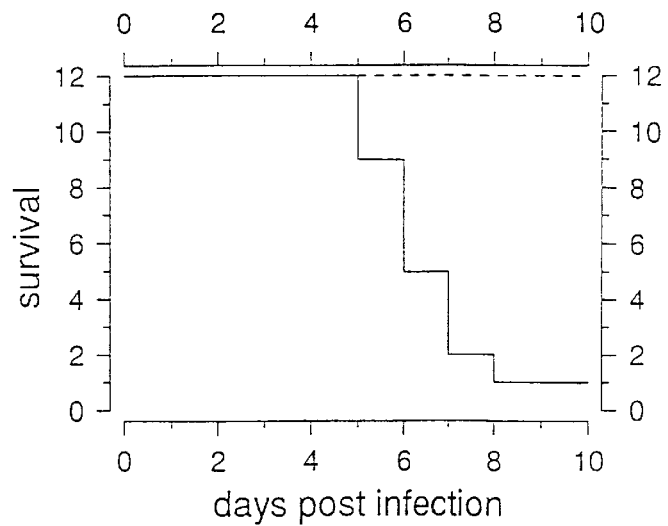
Figure 13B:
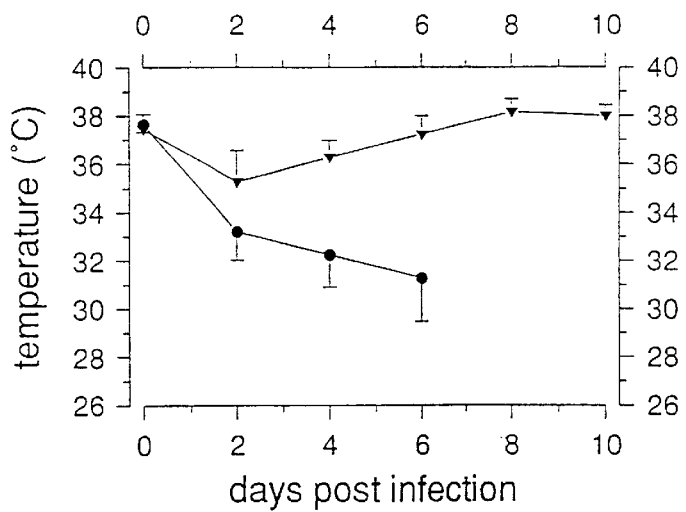
Figure 13C:
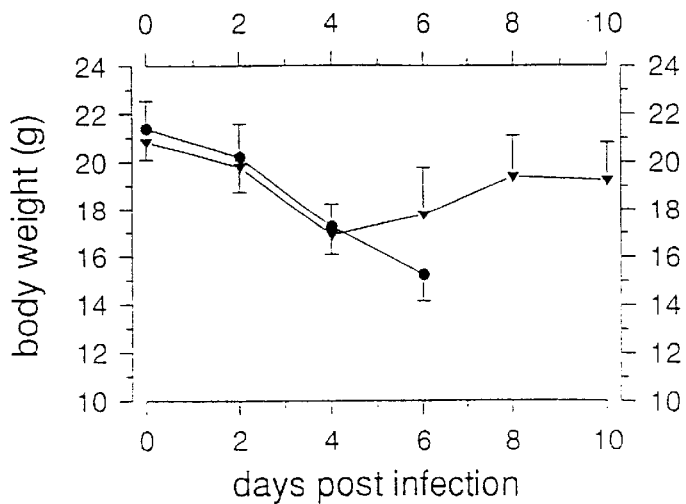
Figure 14A:
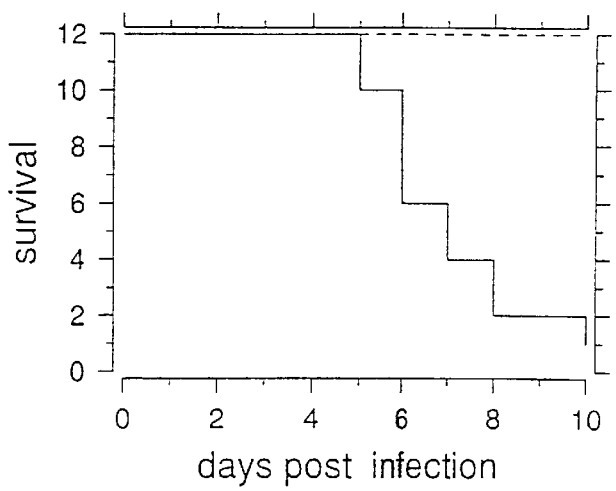
Figure 14B:
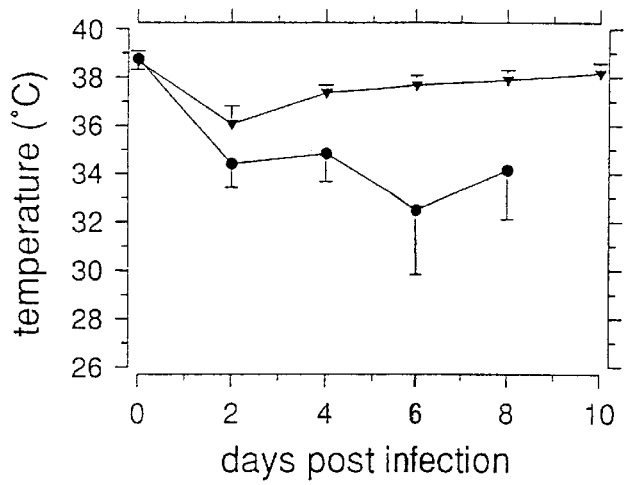
Figure 14C:
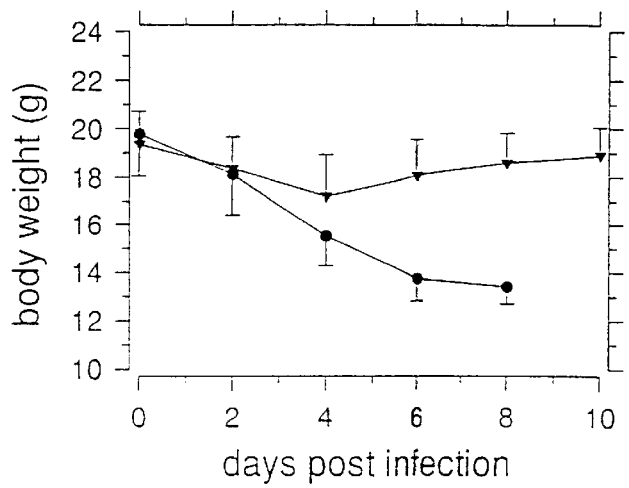
Figure 15:
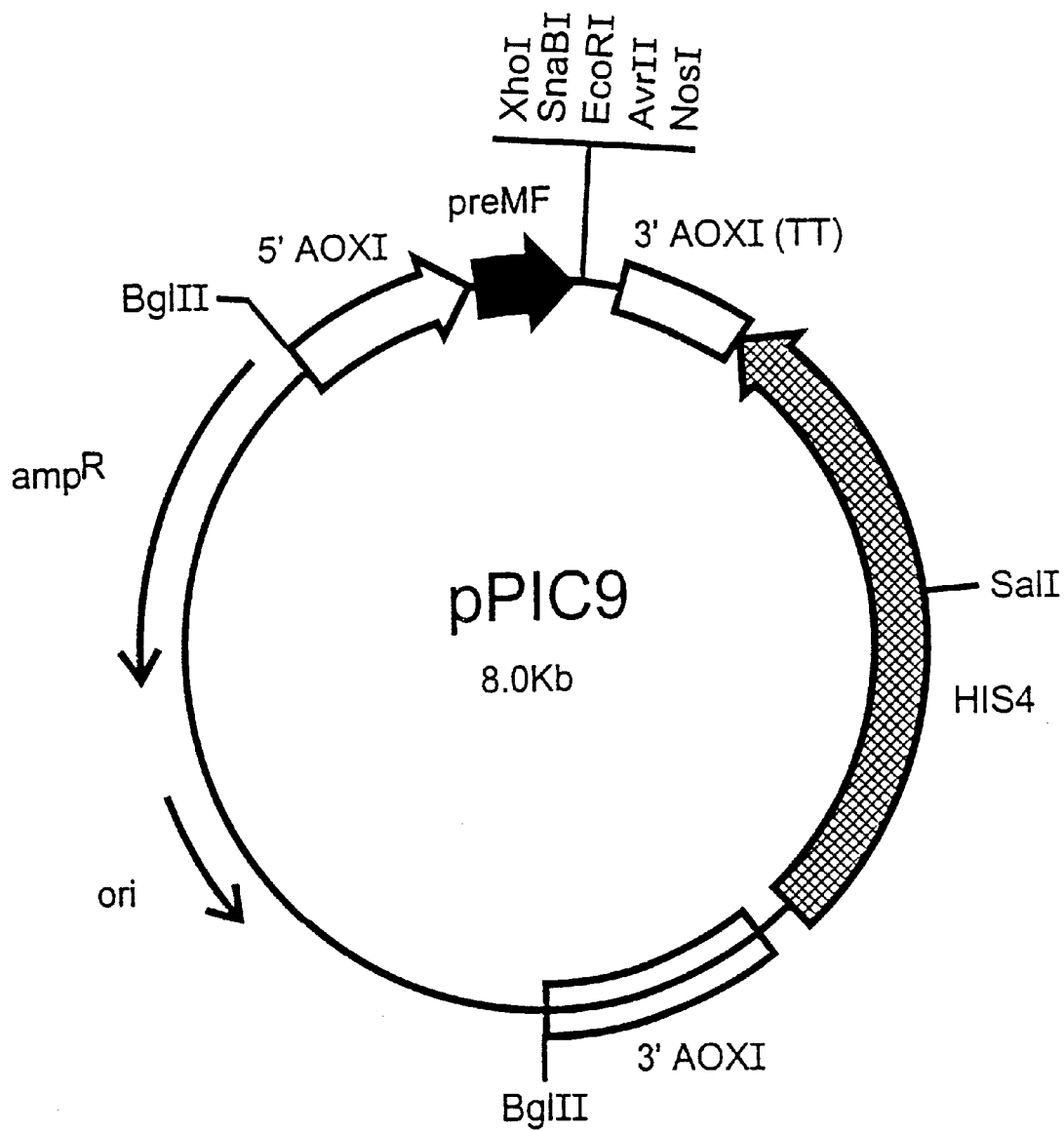
FIG. 15 shows a diagram of the pPIC9 plasmide which contains in addition to the AOXI promoter and terminator sequences the HIS4 marker of *P. pastoris* and the prepro secretion signal of the α-factor gene of *Saccharomyces cerevisiae*. A multiple cloning site is situated behind the secretion signal.
Figure 16:
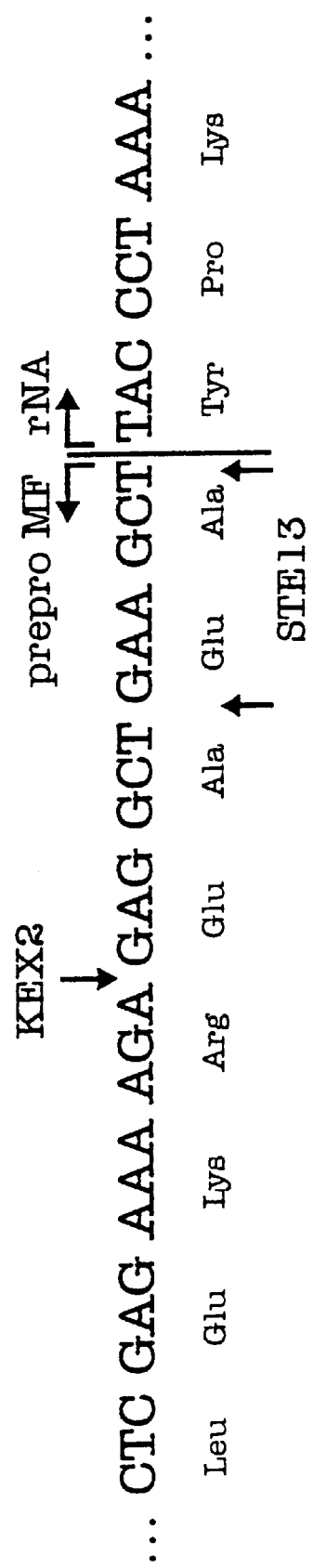
FIG. 16 gives a survey of the fusion region between the prepro secretion signal and the recombinant "hat" part of the neuraminidase. "KEX2" indicates where the propeptide is cleaved in the late Golgi by the endogenous KEX-2 protease. The $(Glu-Ala)_2$ dipeptide is removed by an STE13-type dipeptidyl aminopeptidase. The tyrosine residue does not come from the neuraminidase but is not removed. The following proline corresponds with position 79 of the X-47 neuraminidase.
Figure 17:
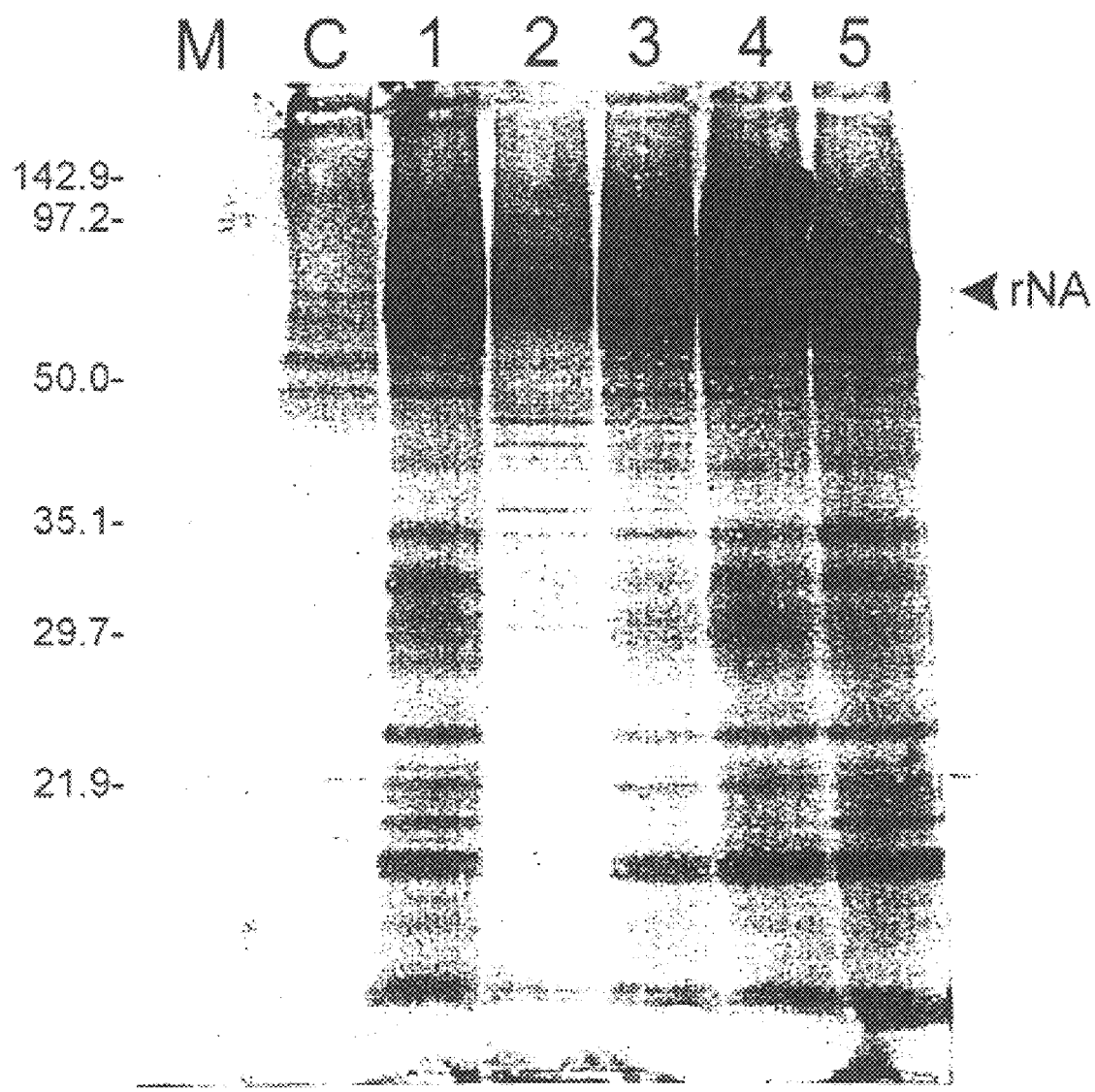
FIG. 17 is a Western blot of a 12.5% polyacrylamide gel with 5 medium samples of individual transformants. Lane 1 contains the medium sample of an untransformed *P. pastoris* strain. The protein material of 1 ml culture medium precipitated with TCA is loaded per lane.

| Steps | Volume ml | Protein mg | Total activity U | Yield % | Specific activity U/mg | Purification -fold |
|---|---|---|---|---|---|---|
| Crude pNA material | 21.0 | 22.1 | 86,000 | 100 | 3,890 | 1.0 |
| Sepharose S | 32.5 | 0.98 | 53,800 | 62.6 | 54,900 | 14.1 |
| Superdex 200 | 12.0 | 0.74 | 42,900 | 49.9 | 58,000 | 14.9 |

The table relates to a single typical purification experiment (see text for details). The volume after Superdex 200 gel filtration shows a pool of two chromatography runs.

TABLE 2

Purification of NAs produced by Sf9 insect cells

| Steps | Volume ml | Protein mg | Total activity U | Yield % | Specific activity U/mg | Purification -fold |
|---|---|---|---|---|---|---|
| Crude medium | 995 | 281 | 144,000 | 100 | 510 | 1.0 |
| (20–60)% $(NH_4)_2SO_4$ precipitate | 99.5 | 97.5 | 117,000 | 81.3 | 1,200 | 2.4 |
| Sepharose Q | 60.0 | 7.27 | 70,300 | 48.9 | 9,670 | 19.0 |
| N-(p-aminophenyl) oxamic acid agrose Superdex 200 | 54.0 | 2.63 | 49,100 | 34.1 | 18,700 | 36.7 |
| tetramer | 8.0 | 0.66 | 36,000 | 25.1 | 54,700 | 107 |
| dimer | 8.0 | 0.98 | — | — | — | — |
| monomer | 8.0 | 0.15 | — | — | — | — |

The table contains a single typical purification experiment (see text for details). The specified volumes after Superdex 200 gel filtration show pools of NAs fractions collected from two chromatography runs.

References

Bentley, D. R. en Brownlee, G. G. Sequence of the N2 neuraminidase from influenza virus A/NT/60/68. Nucl. Acids Res. 10, 5033 (1982)

Blok, J., Air, G. M., Laver, W. G., Ward, C. W., Lilley, G. G., Woods, E. F., Roxburgh, C. M. & Inglis, A. S. (1982) Studies on the size, chemical composition and partial sequence of the neuraminidase (NA) from type A influenza virus show that the N-terminal region of the NA is not processed and serves to anchor the NA in the viral membrane, Virology 119, 109–121.

Bradford, M. M. (1976) A rapid and sensitive method for the quantitation of microgram quantities of protein utilizing the principle of protein-dye binding, Anal. Biochem. 72, 248–254.

Bucher, D. C. (1977) Purification of neuraminidase from influenza viruses by affinity chromatography, Biochim. Biophys. Acta 482, 393–399.

Bucher, D. J. & Kilbourne, E. D. (1972) A2 (N2) neuraminidase of the X-7 influenza virus recombinant: Determination of molecular size and subunit composition of the active unit, J. Virol. 10, 60–66.

Burnet, F. M., Stone, J. D. (1947) The receptor destroying enzyme of *V. cholerae,* Aust. J. Exp. Biol. Med. Sci. 25, 227–233.

Butters, T. D. & Hughes, R. C. (1981) Isolation and characterisation of mosquito cell membrane glycoproteins, Biochim. Biophys. Acta 640, 655–671.

Butters, T. D., Hughes, R. C. & Vischer, P. (1981) Steps in the biosynthesis of mosquito cell membrane glycoproteins and the effects of tunicamycin, Biochim. Biophys. Acta 640, 672–686.

Chong, A. K. J., Pegg, M. S. & Itzstein, M. (1991) Influenza virus sialidase: effect of calcium on steady-state kinetic parameters, Biochim. Biophys. Acta 1077, 65–71.

Colman, P. M., Varghese, J. N. & Laver, W. G. (1983) Structure of the catalytic and antigenic sites in influenza virus neuraminidase, Nature 303, 41–44.

Colman, P. M. & Ward, C. W. (1985) Structure and diversity of influenza neuraminidase, Curr. Top. Microbiol. Imunol. 114, 177255.

Cuatrecasas, P. & Illiano, G. (1971) Purification of neuraminidases from *Vibrio cholerae, Clostridium perfringens* and influenza virus by affinity chromatography, Biochem. Biophys. Res. Commun. 44, 178–184.

Dimmock, N. J. (1971) Dependence of the activity of an influenza virus neuraminidase upon Ca++, J. Gen. Virol. 13, 481–483.

Domingo, D. L. & Trowbridge, S. I. (1988) Characterisation of the human transferrin receptor produced in a baculovirus expression system, J. Biol. Chem. 263, 13386–13392.

Edmond, J. D., Johnston, R. G., Kidd, D., Rylance, H. J. & Sommerville, R. G. (1966) The inhibition of neuraminidase and antiviral action, Br. J. Pharmacol. 27, 415–421.

Fields, S., Winter, G. & Brownlee, G. G. (1981) Structure of the neuraminidase in human influenza virus A/PR/8/34, Nature (Lond.) 290, 213–217.

Gallagher, M., Bucher, D. J., Dourmashkin, R., Davis, J. F., Rosenn, G. & Kilbourne, E. D. (1984) Isolation of immunogenic neuraminidases of human influenza viruses by a combination of genetic and biochemical procedures, J. Clin. Microbiol. 20, 89–93.

Gottschalk, A. (1957) The specific enzyme of influenza virus and *Vibrio cholerae*, Biochim. Biophys. Acta 23, 645–646.

Griffin, J. A. & Compans, R. W., (1979) Effect of cytochalasin B on the maturation of enveloped viruses, J. Exp. Med. 150, 379–391.

Griffin, J. A., Basak, S. & Compans, R. W. (1983) Effects of hexose starvation and the role of sialic acid in influenza virus release, Virology 125, 324–334.

Hirst, G. K. (1942) The quantitative determination of influenza virus and antibodies by means of red cell agglutination, J. Exp. Med. 75, 47–64.

Hsieh, P. & Robbins, P. W. (1984) Regulation of asparagine-linked oligosaccharide processing, J. Biol. Chem. 259, 2375–2382.

Jahiel, R. I. & Kilbourne, E. D. (1966) Reduction in plaque size and reduction in plaque number as differing indices of influenza virus-antibody reaction, J. Bacteriol. 92, 1521–1534.

Jarvris, D. L., Fleming, J. -A. G. W., Kovacs, G. R., Summers, M. D. & Guarino, L. A. (1990) Use of early baculovirus promoters for continuous expression and efficient processing of foreign gene products in stably transformed Lepidopteran cells, Bio/Technology 8, 950–955.

Jarvis, D. L. & Summers, M. D. (1989) Glycosylation and secretion of human tissue plasminogen activator in recombinant baculovirusinfected insect cells, Mol. Cell. Biol. 9, 214–223.

Johansson, B. E., Moran, T. M. & Kilbourne, E. D. (1987) Antigen-presenting B cells and helper T cells cooperatively mediate intravirionic antigenic competition between influenza A virus surface glycoproteins, Proc. Natl. Acad. Sci. USA 84, 6869–6873.

Johansson, B. E., Bucher, D. J. & Kilbourne, E. D. (1989) Purified influenza virus hemagglutinin and neuraminidase are equivalent in stimulation of antibody response but induce contrasting types of immunity to infection, J. virol. 63, 1239–1246.

Johansson, B. E. & Kilbourne, E. D. (1990) comparative long-term effects in a mouse model system of influenza whole virus and purified neuraminidase vaccines followed by sequential infections, J. Infect. Dis. 162, 800–808

Johansson, B. E., Grajower, B. & Kilbourne, E. D. (1993) Infection-permissive immunization with influenza virus neuraminidase prevents weight loss in infected mice, vaccine 11, 1037–1041

Kendal, A. P., Pereira, M. S. & Skehel, J. J. (1982) Concepts and Procedures for Laboratory-based Influenza Surveillance, World Health Organization Collaborating Centers for Reference and Research on Influenza.

Kida, H., Webster, R. B. & Yanagawa, R. (1983) Inhibition of virus-induced hemolysis with monoclonal antibodies to different antigenic areas on the hemagglutinin molecule of A/Seal/Massachusetts/1/80 (H7N7) influenza virus, Arch. Virol. 76, 91–99.

Kilbourne, E. D. (1976) comparative efficacy of neuraminida-sespecific and conventional influenza virus vaccines in induction of antibody to neuraminidase in humans, J. Infect. Dis. 134, 384–394.

Kilbourne, E. D., Laver, W. G., Schulman, J. L. & Webster, R. G. (1968) Antiviral activity of antiserum specific for an influenza virus neuraminidase, T. virol. 2, 281–288.

Kuroda, K, Hauser, C., Rott, R., Klenk, H. -D. & Doerfler, W. (1986) Expression of the influenza virus haemagglutinin in insect cells by a baculovierus vector, EMBO J. 5, 1359–1365.

Kuroda, K., Geyer, H., Geyer, R., Doerfler, W. & Klenk, H. -D. (1990) The oligosaccharides of influenza virus hemagglutinin expressed in insect cells by a baculovirus vector, Virololy 174, 418–429.

Laemmli, U. K. (1970) Cleavage of structural proteins during the assembly of the head of bacteriophage T4, Nature (London) 227, , 680–685.

Laver, W. G. (1978) Crystallisation and peptide maps of neuraminidase "heads" from H2N2 and H3N2 influenza virus strains, Virology 86, 78–87.

Laver. W. G. & Valentine, R. C. (1969) Morphology of the isolated haemagglutinin and neuraminidase subunits of influenza virus, virology 38, 105–119.

Luckow, V. A. & Summers, M. D. (1988) Trends in the development of baculovirus expression vectors, Bio/Technology 6, 47–55.

Luckow, V. A. & Summers, M. D. (1989) High level expression of nonfused foreign genes with *Autographa californica* nuclear polyhedrosis virus expression vectors, Virology 170, 31–39.

Mayron, L. W., Robert, B., Winzler, R. J. & Rafelson, M. E. (1961) Studies on the neuraminidase of influenza virus. I. Separation and some properties of the enzyme from Asian and PR8 strains, Arch. Biochem. Biophys. 92, 475–483.

Min Jou, W., Verhoeyen, M., Devos, R., Saman, E., Fang, R., Huylebroeck, D. & Fiers, W. (1980) Complete structure of the hemagglutinin gene from the human influenza A/Victoria/3/75 (H3N2) strain as determined from cloned DNA, Cell 19, 683–696.

Morrisey, J. H. (1981) Silver stain for proteins in polyacrylamide gels: a modified procedure with enhanced uniform sensitivity, Anal. Biochem. 117, 307–310.

Potier, M., Mameli, L., Bélisle, M., Dallaire, L. & Melancon, S. B. (1979) Fluorometric assay of neuraminidase with a sodium (4-methylumbelliferyl-α-D-N-aCetylneuraminate) substrate, Anal. Biochem. 94, 287–296.

Rott, R., Becht, H. & Orlich, M. (1974) The significance of influenza virus neuraminidase in immunity, J. Gen. Virol. 22, 35–41.

Schulman, J. L., Khakpour, M. & Kilbourne, E. D. (1968) Protective effects of specific immunity to viral neuraminidase on influenza virus infection of mice, J. Virol. 2, 778–786.

Seto, J. T., Drzeniek, R. & Rott R. (1966) Isolation of a low molecular weight sialidase (neuraminidase) from influenza virus, Biochim. Biophys. Acta 113, 402–404.

Summers, M. D. & Smith, G. E. (1987) A Manual of Methods for Baculovirus Vectors and Insect Cell Culture Procedures, Texas Agricultural Experiment stations Bulletins No. 1555.

van Drunen Littel, S., Parker, M. D., Fitzpatrick, D. R., Zamb, T. J., van den Hurk, J. V., Campos, M., Harland, R.

& Babiuk, L. A. (1991) Expression of bovine herpersvirus 1 glycoprotein gIV by recombinant baculovirus and analysis of its immunogenic properties, J. Virol. 65, 263–271.

Van Rompuy, L., Min Jou, W., Huylebroeck, D. & Fiers, W. (1982) Complete nucleotide sequence of a human influenza gene of subtype N2 (A/Vic/3/75), J. Mol. Biol. 161, 1–11.

Varghese, J. N., Laver, W. C. & Colman, P. M. (1983) Structure of the influenza virus glycoprotin antigen neuraminidase at 2.9 Å resolution, Nature (Lond.) 303, 35–40.

Varghese, J. N. & Colman, P. M. (1991) Three-dimensional structure of the neuraminidase of influenza virus A/Tokyo/3/67 at 2.2 Å resolution, J. Mol. Biol. 221, 473–486.

Ward, C. W., Colman, P. M. & Laver, W. G. (1983) The disulphide bonds of an Asian influenza virus neuraminidase, FEBS Lett. 153, 29–30.

Ward, C. W., Elleman, T. C. & Azad, A. A. (1982) Amino Acid sequence of the pronase-released heads of neuraminidase subtype N2 from the Asian strain A/Tokyo/3/67 of influenza virus, Biochem. J. 207, 91–95.

Webster, R. G., Hinshaw, V. S. & Laver, W. G. (1982) Selection and analysis of antigenic variants of the neuraminidase of N2 influenza viruses with monoclonal antibodies, Virology 117, 93–104.

Webster, R. G., Reay, P. A. & Laver, W. G. (1988) Protection against lethal influenza with neuraminidase, Virology 164, 230–237.

Wilson, V. W. & Rafelson M. E. (1963) Isolation of neuraminidase from influenza virus, Biochem. Prep. 10, 113–117.

Wrigley, N. G., Laver, W. G. & Downie, J. C. (1977) Binding of antibodies to isolated haemagglutinin and neuraminidase molecules of influenza virus observed in the electron microscope, J. Mol. Biol. 109, 405–421.

Wrigley, N. G., Skehel, J. J., Charlwood, P. A. & Brand, C. M. (1973) The size and shape of influenza virus neuraminidase, virology 51, 525–529.

Couch, R. B., Douglas, R. G. Jr., Fredson, D. S. & Kasel, J. A. Correlation studies of a recombinant influenza-virus vaccine. III. Protection against experimental virus in man. J. Infect. Dis. 1971, 124, 473

Ogra, P. L., Chow, T., Beutner, K. R., Rubi, E., Strussenberg, J., DeMello S. & Rizzone C. Clinical and immunological evaluation of neuraminidase-specific influenza A virus in humans. J. Infect. Dis. 1977, 135, 499

Kilbourne, E. D. comparative efficacy of neuraminidase-specific and conventional influenza virus vaccines in the induction of antibody to neuraminidase in humans. J. Infect. Dis. 1976, 134, 384

Kilbourne, E. D., Cerini, C. P., Khan, M. W., Mitchell, J. W. Jr. & Ogra, P. L. Immunologic response to the influenza virus neuraminidase is influenced by prior experience with the associated viral hemagglutinin. I. Studies in human vaccinees. J. Immunol. 1987, 138, 3010

Johansson, B. E., Moran, T. W., Bona, C. B., Popple, S. W. & Kilbourne, E. D. Immunologic response to influenza virus neuraminidase is influenced by prior experience with the associated viral hemagglutinin. II. Sequential infection of mice simulates human experience. J. Immunol. 1987, 139, 2010

Johansson, B. E., Moran, T. M., Constantin, A. B. & Kilbourne, E. D. Immunologic response to influenza virus neuraminidase is influenced by prior experience with the associated viral hemagglutinin. III. Reduced generation of neuraminidase-specific helper T cells in hemagglutinin-primed mice. J. Immunol. 1987, 139, 2015

Hirst, G. K. The quantitative determination of influenza virus and antibodies by means of red cell agglutination. J. Exp. Med. 1942, 75, 47

Davenport, F. M., Hennessy, A. V., Brandon, F. M., Webster, R. G., Barrett, C. D. & Lease, G. O. Comparisons of serological and febrile responses in humans to vaccination with influenza A viruses or their hemagglutinins. J. Lab. Clin. Med. 1964, 63, 5

Kida, H., Webster, R. G. & Yanagawa, R. Inhibition of virus-induced hemolysis with monoclonal antibodies to different antigenic areas on the hemagglutinin molecule of A/Seal/Massachusetts/1/80 (H7N7) influenza virus. Arch. Virol. 1983, 76, 91

Jahiel, R. I. & Kilbourne, E. D. Reduction in plaque size and reduction in plaque number as differing indices of influenza virus-antibody reactions. J. Bacteriol. 1966, 92, 1521

Kilbourne, E. D., Laver, W. G., Schulman, J. L. & Webster, R. G. Antiviral activity of antiserum specific for an influenza virus neuraminidase. J. Virol. 1968, 2, 281

Johansson, B. E., Bucher, D. J. & Kilbourne, E. D. Purified influenza virus hemagglutinin and neuraminidase are equivalent in stimulation of antibody response but induce contrasting types of immunity. J. Virol. 1989, 63, 1239

Schulman, J. L., Khakpour, M. & Kilbourne, E. D. Protective effects of specific immunity to viral neuraminidase on influenza virus infection of mice. J. Virol. 1968, 2, 778

Johansson, B. E. & Kilbourne, E. D. comparative long-term effects in a mouse model system of influenza whole virus and purified neuraminidase vaccines followed by sequential infections. J. Infect. Dis. 1990, 162, 800

Johansson, B. E., Moran, T. M. & Kilbourne, E. D. Antigen-presenting B cells and helper T cells cooperatively mediate intravirionic antigenic competition between influenza A virus surface glycoproteins, Proc. Natl. Acad. Sci. 1987, 84, 6869

Rott, R., Becht, H. & Orlich, M. The significance of influenza virus in immunity. J. Gen. Virol. 1974, 22, 35

Webster, R. G., Reay, P. A. & Laver, W. G. Protection against lethal influenza with neuraminidase. Virology 1988, 164, 230

Johansson, B. E., Grajower, B. & Kilbourne, E. D. Infection-permissive immunization with influenza virus neuraminidase prevents weight loss in infected mice. Vaccine 1993, 11, 1037

Kilbourne, E. D., Palese, P. & Schulman, J. L. Inhibition of viral neuraminidase as a new approach to the prevention of influenza. In Perspectives in virology. Vol 9 (Ed. Pollard, M.) New York, Academic Press, 1975, 99–113

Kilbourne, E. D. Immunization strategy: infection-permissive vaccines for the modulation of infection. In Modern approaches to vaccines (Eds. Chanock R. M., Lerner, R. A.) Cold Spring Harbor Laboratory, Cold Spring Harbor, N.Y., 1984, 269–274

Vanlandschoot, P., Maertens, G., Min Jou, W. & Fiers, W. Recombinant secreted hemagglutinin protects mice against a lethal challenge of influenza virus. Vaccine 1993, 11, 1185

Brown,, J. & Laver, W. G. The effect of antineuraminidase antibody on the elution of influenza virus from cells. J. Gen. Virol. 1968, 2, 291

Gallagher, M., Bucher, D. J., Dourmashkin, R., Davis, J. F., Rosenn, G. & Kilbourne E. D. Isolation of immunogenic neuraminidase of human influenza viruses by a combination of genetic and biochemical procedures. J. Clin. Microbiol. 1984, 20, 89

Colman, P. M. & Ward, C. W. Structure and diversity of influenza neuraminidase. Curr. Top. Microbiol. Imunol. 1985, 114, 177

Kilbourne, E. D. *Influenza*. Plenum, New York, 1987

Van Rompuy, L., Min Jou, W., Huylebroeck, D. & Fiers, , W. Complete nucleotide sequence of a human influenza neuraminidase gene of subtype N2 (A/Vic/3/75). J. Mol. Biol. 1982, 161, 1

Lentz, M. R., Air, G. M., Laver, W. G. & Webster, R. G. Sequence of the neuraminidase gene from influenza virus A/Tokyo/3/67 and previously uncharacterised monoclonal variants. Virology 1984, 135, 257

Kawaoka, Y., Yamnikova, S., Chambers, T. M., Lvov, D. K. & Webster, R. G. Molecular characterization of a new hemagglutinin, subtype 14, of influenza A virus. Virology 1990, 179, 759

Baez, M., Palese, P. & Kilbourne, E. D. Gene composition of high-yielding influenza vaccine strains obtained by recombination. J. Infect. Dis. 1980, 141, 362 tor or infected with a virus which is transformed with a neuraminidase expression vector, wherein the expression vector comprises the coding region of a neuraminidase gene of an influenza virus corresponding to the C-terminal 440 amino acids, or a modified version thereof, having antigenic properties corresponding with naturally occurring neuraminidase, preceded in phase by a type I signal sequence; and b) isolating the expression product neuraminidase from the culture medium.

2. Recombinant influenza NA2 neuraminidase in substantially isolated form, obtainable by culturing in a suitable culture medium host cell infected with a virus which is transformed by double homologous recombination of its genome with the recombinant expression vector pAc2IVNAs (LMBP 2976) and isolating the expression product neuraminidase from the culture medium.

3. Recombinant influenza neuraminidase as claimed in claim 1, characterized in that the host cells are insect cells.

4. Recombinant influenza neuraminidase as claimed in claim 3, characterized in that the insect cells are sf9 insect cells.

5. Vector for expressing a secretable influenza neuraminidase comprising:

a) a part of the coding region of the influenza neuraminidase gene corresponding to the C-terminal 440 amino acids, or modified versions thereof having antigenic properties corresponding with naturally occurring neuraminidase;

b) a type I signal sequence located at 5' from the coded region and coupled in phase thereto;

c) a promoter located at 5' from the signal sequence; and d) a transcription terminator located at 3' from the coding region.

6. Vector as claimed in claim 5, characterized in that the signal sequence originates from the hemagglutinin gene of the influenza NA2 virus A/Victoria/3/75 (H3N2).

7. Vector as claimed in claim 5, characterized in that the promoter is a polyhedrine promoter.

We claim:

1. Recombinant neuraminidase free of hemagglutinin, influenza viral RNA or other influenza virus components, obtainable by:

a) culturing in a suitable culture medium host cells which are transformed with a neuraminidase expression vec- 8. Vector as claimed in claim 5, characterized in that the transcription terminator originates from SV40 and/or the polyhedrine gene.

9. Vector pAc2IVNAs with the deposit accession number LMBP 2976.

10. Method for manufacturing a recombinant influenza neuraminidase comprising the steps of:

a) constructing an expression vector comprising a type I signal sequence and coupled thereto in phase a sequence corresponding to the C-terminal 424 amino acids of the coding region of the A/Victoria/3/75 influenza neuraminidase gene, this under the regulation of suitable promoter and terminator sequence wherein the expression vector does not include in phase with and immediately preceding the neuraminidase coding region a membrane anchor sequence corresponding to the N-terminal 45 amino acids of the neuraminidase gene, such that the membrane anchor function of the N-terminal 45 amino acids is not retained;

b) transforming a host cell with the thus obtained expression vector;

c) culturing the transformed host cell in a culture medium under conditions enabling the expression of the recombinant neuraminidase; and d) isolating the recombinant neuraminidase from the culture medium.

11. Method for manufacturing a recombinant influenza NA2 neuraminidase comprising the steps of:

a) constructing a vector comprising an expression module consisting of a type I signal sequence and coupled thereto in phase a sequence corresponding to the C-terminal 424 amino acids of the coding region of the influenza NA2 neuraminidase gene of the virus strain A/Victoria/3/75 , this under the regulation of suitable promoter and terminator sequences for transcription;

b) bringing the expression module of the vector by means of double homologous recombination into the genome of a baculovirus in order to obtain a recombinant baculovirus;

c) infecting a host cell with the recombinant baculovirus;

d) culturing the infected host cell in a culture medium under conditions enabling the expression of the recombinant neuraminidase; and e) isolating the recombinant neuraminidase from the culture medium.

12. Method for manufacturing a recombinant influenza NA2 neuraminidase comprising the steps of:

a) transforming a baculovirus with the expression module of the vector PAc2IVNAs with the deposit accession number LMBP 2976 by means of double homologous recombination;

b) infecting a host cell with the thus obtained recombinant baculovirus;

c) culturing the infected host cell in a culture medium under conditions enabling the expression of the recombinant neuraminidase; and d) isolating the recombinant neuraminidase from the culture medium.

13. Recombinant neuraminidase free of hemagglutinin, influenza viral RNA or other influenza virus components, obtained by:

a) culturing in a suitable culture medium host cells which are transformed with a neuraminidase expression vector or infected with a virus, the expression vector and the virus include a neuraminidase expression vector, wherein the expression vector comprises the coding region of a neuraminidase gene of an influenza virus corresponding to the C-terminal 424 amino acids, or a modified version thereof having antigenic properties corresponding with naturally occurring neuraminidase, preceded in phase by a type I signal sequence, wherein the expression vector or virus does not include in phase with and immediately preceding the neuraminidase coding region a membrane anchor sequence corresponding to the N-terminal 45 amino acids of the neuraminidase gene such that the membrane anchor function of the N-terminal 45 amino acids are retained; and b) isolating the expression product neuraminidase from the culture medium.

* * * * *

UNITED STATES PATENT AND TRADEMARK OFFICE
CERTIFICATE OF CORRECTION

PATENT NO. : 5,962,298    Page 1 of 3
DATED     : October 5, 1999
INVENTOR(S): Walter Charles Fiers et al.

It is certified that error appears in the above-identified patent and that said Letters Patent is hereby corrected as shown below:

Title Page, under [56] References Cited, OTHER PUBLICATIONS, insert:
--Mather et al. (1992) Expression of influenze neuraminidase in baculovirus-infected cells. Virus Research 26: 127-139, Nov. 1992.
Lin et al. (1992) Expression of neuraminidase of influenza A virus in insect cells. Shengwu Huaxue Yu Shengwu Wuli Xuebao 24(3): 201-205.
Johansson et al. (1990) Comparative long-term effects in a mouse model system of influenza whole virus and purified neuraminidase vaccines followed by sequential infections. Journal of Infectious Diseases 162: 800-809.
Johansson et al. (1989) Purified influenza virus hemagglutinin and neuraminidase are equivalent in stimulation of antibody response but induce contrasting types of immunity to infection. Journal of Virology 63(3): 1239-1246.--.

Title Page, [75] Inventors: "Tom Marie Deroo" should read --Tom Maria Deroo--.

Column 1 Line 40 "$(M_x$" should read --$(M_r$--.

Column 3 Line 54 "factor a" should read --factor $\alpha$--.

Column 5 Line 48 "buffer C: 10 mm" should read --buffer C: 10 mM--.

Column 6 Line 54 "(2.9 kd)" should read --(29 kd)--.

Column 7 Line 4 "$\beta$-cation" should read --S-cation--.

Column 12 Line 35 "an a gel" should read --on a gel--.

UNITED STATES PATENT AND TRADEMARK OFFICE
CERTIFICATE OF CORRECTION

PATENT NO.   : 5,962,298
DATED        : October 5, 1999
INVENTOR(S)  : Walter Charles Fiers et al.

It is certified that error appears in the above-identified patent and that said Letters Patent is hereby corrected as shown below:

Column 16 Line 39 "6, whereafter" should read --8, whereafter--.

Column 18 Line 67 "$Gln_1$" should read --$Gln_{17}$--.

Column 22 Line 13 "Bucher, D.C." should read --Bucher, D.J.--.

Column 24 Line 3 "T. virol." should read --J. virol.--.

Column 24 Line 20 "Laver." should read --Laver,--.

Column 28 Line 3, Claim 1, "the coding region" should read --a coding region--.

Column 28 Line 4, Claim 1, "influenza virus corresponding" should read --influenza virus A/Victoria/3/75 corresponding--.

Column 28 Lines 5-6, Claim 1, "C-terminal 440 amino acids, or a modified version thereof, having" should read --C-terminal 424 amino acids of the neuraminidase, having--.

Column 28 Line 8, Claim 1, "signal sequence; and" should read --signal sequence wherein the expression vector or virus does not include in phase with and immediately preceding the neuraminidase coding region a membrane anchor sequence corresponding to the N-terminal 45 amino acids of the neuraminidase gene, such that the membrane anchor function of the N-terminal 45 amino acids is not retained; and--.

Column 28 Line 25, Claim 5, "a) a part of the coding region" should read --a) a coding region--.

Column 28 Line 25, Claim 5, "of the influenza" should read --of the A/Victoria/3/75 influenza--.

UNITED STATES PATENT AND TRADEMARK OFFICE
CERTIFICATE OF CORRECTION

PATENT NO. : 5,962,298
DATED : October 5, 1999
INVENTOR(S) : Walter Charles Fiers et al.

It is certified that error appears in the above-identified patent and that said Letters Patent is hereby corrected as shown below:

Column 28 Lines 26-27, Claim 5, "C-terminal 440 amino acids, or modified versions thereof having" should read --C-terminal 424 amino acids, having--.

Column 28 Lines 30-31 "from the coded region" should read --from the neuraminidase coding region--.

Column 28 Line 35, Claim 5, "region." should read --region, wherein the expression vector does not include in phase with and immediately preceding the neuraminidase coding region a membrane anchor sequence corresponding to the N-terminal 45 amino acids of the neuraminidase gene, such that the membrane anchor function of the N-terminal 45 amino acids is not retained.--.

Column 30 Line 35 "are retained" should read --is not retained--.

Signed and Sealed this

Twenty-eighth Day of November, 2000

Attest:

Q. TODD DICKINSON

Attesting Officer

Director of Patents and Trademarks